US 8,337,868 B2

(12) United States Patent
Lotan et al.

(10) Patent No.: US 8,337,868 B2
(45) Date of Patent: *Dec. 25, 2012

(54) STINGING CELLS EXPRESSING AN EXOGENOUS POLYNUCLEOTIDE ENCODING A THERAPEUTIC, DIAGNOSTIC OR A COSMETIC AGENT AND METHODS COMPOSITIONS AND DEVICES UTILIZING SUCH STINGING CELLS OR CAPSULES DERIVED THEREFROM FOR DELIVERING THE THERAPEUTIC, DIAGNOSTIC OR COSMETIC AGENT INTO A TISSUE

(75) Inventors: Tamar Lotan, Jordan Valley (IL); Shimon Eckhouse, Haifa (IL); Esther Shaoul, Nesher (IL)

(73) Assignee: NanoCyte Inc., Wilmington, DE (US)

( * ) Notice: Subject to any disclaimer, the term of this patent is extended or adjusted under 35 U.S.C. 154(b) by 396 days.

This patent is subject to a terminal disclaimer.

(21) Appl. No.: 12/588,368

(22) Filed: Oct. 14, 2009

(65) Prior Publication Data
US 2010/0111869 A1 May 6, 2010

Related U.S. Application Data

(62) Division of application No. 10/507,692, filed as application No. PCT/IL03/00241 on Mar. 20, 2003, now Pat. No. 7,611,723.

(60) Provisional application No. 60/367,261, filed on Mar. 26, 2002.

(51) Int. Cl.
*A61K 9/00* (2006.01)
*C07H 21/04* (2006.01)
*C07K 1/00* (2006.01)

(52) U.S. Cl. ........ 424/400; 536/23.1; 536/24.5; 530/350
(58) Field of Classification Search ........................ None
See application file for complete search history.

(56) References Cited

U.S. PATENT DOCUMENTS

| 3,321,188 | A | 5/1967 | Unger |
| 3,839,153 | A | 10/1974 | Schuurs et al. |
| 3,850,578 | A | 11/1974 | McConnell |
| 3,850,752 | A | 11/1974 | Schuurs et al. |
| 3,853,987 | A | 12/1974 | Dreyer |
| 3,879,262 | A | 4/1975 | Schuurs et al. |
| 3,984,533 | A | 10/1976 | Uzgiris |
| 4,034,074 | A | 7/1977 | Miles |
| 4,666,828 | A | 5/1987 | Gusella |
| 4,801,531 | A | 1/1989 | Frossard |
| 5,073,488 | A | 12/1991 | Matner et al. |
| 5,162,378 | A | 11/1992 | Guthauser |
| 5,192,659 | A | 3/1993 | Simons |
| 5,272,057 | A | 12/1993 | Smulson et al. |
| 5,362,442 | A | 11/1994 | Kent |
| 5,641,508 | A | 6/1997 | Li et al. |
| 5,885,211 | A | 3/1999 | Eppstein et al. |
| 5,885,260 | A | 3/1999 | Mehl, Sr. et al. |
| 6,019,967 | A | 2/2000 | Breton et al. |
| 6,022,316 | A | 2/2000 | Eppstein et al. |
| 6,132,747 | A | 10/2000 | Lotan |
| 6,338,837 | B1 | 1/2002 | Lotan |
| 6,406,709 | B1 | 6/2002 | Lotan |
| 6,416,960 | B1 | 7/2002 | Bryan |
| 6,596,531 | B2 | 7/2003 | Campbell et al. |
| 6,613,344 | B2 | 9/2003 | Lotan et al. |
| 6,613,744 | B2 | 9/2003 | Wozney et al. |
| 6,923,976 | B2 | 8/2005 | Lotan et al. |
| 7,338,665 | B2 | 3/2008 | Lotan et al. |
| 8,062,660 | B2 | 11/2011 | Lotan et al. |
| 2001/0004715 | A1 | 6/2001 | Duran et al. |
| 2002/0039592 | A1 | 4/2002 | Lotan et al. |
| 2003/0189850 | A1 | 10/2003 | Sasaki et al. |
| 2003/0202995 | A1 | 10/2003 | Lotan et al. |
| 2004/0224013 | A1 | 11/2004 | Lotan et al. |
| 2004/0235143 | A1 | 11/2004 | Sasaki et al. |
| 2005/0181978 | A1 | 8/2005 | Rojkjaer et al. |
| 2006/0039897 | A1 | 2/2006 | Lotan et al. |
| 2006/0099272 | A1 | 5/2006 | Lotan |
| 2006/0099273 | A1 | 5/2006 | Lotan |
| 2006/0159769 | A1 | 7/2006 | Lotan et al. |
| 2006/0234203 | A1 | 10/2006 | Lotan et al. |
| 2007/0160546 | A1 | 7/2007 | Lotan et al. |
| 2010/0055058 | A1 | 3/2010 | Lotan et al. |
| 2011/0070224 | A1 | 3/2011 | Lotan et al. |
| 2011/0250245 | A1 | 10/2011 | Lotan et al. |

FOREIGN PATENT DOCUMENTS

| EP | 1519755 | 4/2005 |
| WO | WO 98/29134 | 7/1998 |
| WO | WO 99/44507 | 9/1999 |
| WO | WO 99/44508 | 9/1999 |
| WO | WO 99/44637 | 9/1999 |
| WO | WO 99/44638 | 9/1999 |
| WO | WO 00/03758 | 1/2000 |
| WO | WO 00/04821 | 2/2000 |
| WO | WO 00/04832 | 2/2000 |
| WO | WO 00/15102 | 3/2000 |
| WO | WO 01/37778 | 5/2001 |
| WO | WO 02/26191 | 4/2002 |
| WO | WO 03/079967 | 10/2003 |
| WO | WO 2006/048864 | 5/2006 |
| WO | WO 2006/048865 | 5/2006 |
| WO | WO 2006/090367 | 8/2006 |
| WO | WO 2006/111960 | 10/2006 |
| WO | WO 2006/048865 | 11/2006 |

OTHER PUBLICATIONS

Office Action Dated Feb. 27, 2011 From the Israeli Patent Office Re.: Application No. 164191 and Its Translation Into English.
Official Action Dated Oct. 19, 2011 From the US Patent and Trademark Office Re. U.S. Appl. No. 13/166,877.
Official Action Dated Sep. 21, 2011 From the US Patent and Trademark Office Re. U.S. Appl. No. 12/955,990.

(Continued)

Primary Examiner — Tracy Vivlemore

(57) ABSTRACT

A stinging cell comprising an exogenous polynucleotide capable of expressing a therapeutic, cosmetic or diagnostic agent in the stinging cell is provided.

15 Claims, 5 Drawing Sheets
(1 of 5 Drawing Sheet(s) Filed in Color)

OTHER PUBLICATIONS

Response Dated Oct. 17, 2011 to Official Action of Sep. 21, 2011 From the US Patent and Trademark Office Re. U.S. Appl. No. 12/955,990.
Official Action Dated Oct. 4, 2007 From the US Patent and Trademark Office Re.: U.S. Appl. No. 10/507,692.
Böttger et al. "GFP Expression in Hydra: Lessons From the Particle Gun", Development of Gene Evolution, 212: 302-305, 2002.
Murate et al. "Hydra Regeneration From Recombinant Ectodermal and Endodermal Tissue—II. Differential Stability in the Ectodermal and Endodermal Epithelial Organization", Journal of Cell Science, 110: 1155-1164, 1997.
Response Dated Nov. 21, 2011 to Official Action of Oct. 19, 2011 From the US Patent and Trademark Office Re. U.S. Appl. No. 13/166,877.
Official Action Dated Jan. 9, 2012 From the US Patent and Trademark Office Re. U.S. Appl. No. 12/955,990.
Official Action Dated Dec. 21, 2011 From the US Patent and Trademark Office Re. U.S. Appl. No. 13/166,877.
Notice of Allowance Dated Mar. 24, 2011 From the US Patent and Trademark Office Re.: U.S. Appl. No. 12/616,801.
Response Dated Aug. 10, 2010 to Phone Conversation of Aug. 1, 2010 With the Examiner Re. Application No. 155097.
Response Dated Aug. 10, 2010 to Phone Conversation of Aug. 1, 2010 With the Examiner Re. Application No. 199236.
"Skin, Hair, and Nails", http://web.archive.org/web.20030404084846/www.kidshealth.org/PageManager.jsp?dn=Kidshealth&lic=1&ps=107&cat_id-20090&article_set-20552, p. 1-7, 2003.
Communication Pursuant to Article 94(3) EPC Dated Dec. 17, 2008 From the European Patent Office Re.: Application No. 01976586.6.
International Preliminary Report on Patentability Dated Dec. 11, 2008 From the International Bureau of WIPO Re.: Application No. PCT/IL2006/000465.
International Preliminary Report on Patentability Dated May 18, 2007 From the International Bureau of WIPO Re.: Application No. PCT/IL2005/001127.
International Search Report Dated Jun. 22, 2006 From the International Searching Authority Re.: Application No. PCT/IL05/01127.
International Search Report Dated Jun. 24, 2008 From the International Searching Authority Re.: Application No. PCT/IL2006/000465.
Notice of Allowance Dated Aug. 6, 2009 From the US Patent and Trademark Office Re.: U.S. Appl. No. 11/328,221.
Notice of Allowance Dated Jun. 19, 2009 From the US Patent and Trademark Office Re.: U.S. Appl. No. 10/507,692.
Office Action Dated Feb. 15, 2009 From the Israeli Patent and Trademark Office Re.: Application No. 155097 and Its Translation Into English.
Response Dated Dec. 9, 2009 to Official Action of Jul. 10, 2009 From the US Patent and Trademark Office Re.: U.S. Appl. No. 11/108,662.
Official Action Dated Nov. 1, 2007 From the US Patent and Trademark Office Re.: U.S. Appl. No. 11/328,221.
Official Action Dated Oct. 4, 2006 From the US Patent and Trademark Office Re.: U.S. Appl. No. 10/868,802.
Official Action Dated Apr. 6, 2009 From the US Patent and Trademark Office Re.: U.S. Appl. No. 11/374,969.
Official Action Dated Jun. 6, 2006 From the US Patent and Trademark Office Re.: U.S. Appl. No. 10/981,522.
Official Action Dated Aug. 8, 2006 From the US Patent and Trademark Office Re.: U.S. Appl. No. 11/374,969.
Official Action Dated Aug. 9, 2007 From the US Patent and Trademark Office Re.: U.S. Appl. No. 11/374,969.
Official Action Dated Oct. 9, 2008 From the US Patent and Trademark Office Re.: U.S. Appl. No. 11/328,221.
Official Action Dated Jul. 10, 2008 From the US Patent and Trademark Office Re.: U.S. Appl. No. 11/108,662.
Official Action Dated Apr. 13, 2009 From the US Patent and Trademark Office Re.: U.S. Appl. No. 11/328,221.
Official Action Dated Aug. 13, 2007 From the US Patent and Trademark Office Re.: U.S. Appl. No. 11/108,662.
Official Action Dated Dec. 15, 2006 From the US Patent and Trademark Office Re.: U.S. Appl. No. 11/328,221.
Official Action Dated Jul. 17, 2008 From the US Patent and Trademark Office Re.: U.S. Appl. No. 11/328,221.
Official Action Dated Nov. 17, 2008 From the US Patent and Trademark Office Re.: U.S. Appl. No. 10/507,692.
Official Action Dated Feb. 20, 2008 From the US Patent and Trademark Office Re.: U.S. Appl. No. 11/374,969.
Official Action Dated Sep. 20, 2007 From the US Patent and Trademark Office Re.: U.S. Appl. No. 10/981,522.
Official Action Dated Jan. 24, 2008 From the US Patent and Trademark Office Re.: U.S. Appl. No. 10/507,692.
Official Action Dated Apr. 25, 2008 From the US Patent and Trademark Office Re.: U.S. Appl. No. 10/981,498.
Official Action Dated Jul. 26, 2007 From the US Patent and Trademark Office Re.: U.S. Appl. No. 10/981,498.
Official Action Dated Feb. 27, 2007 From the US Patent and Trademark Office Re.: U.S. Appl. No. 11/374,969.
Official Action Dated Mar. 27, 2009 From the US Patent and Trademark Office Re.: U.S. Appl. No. 10/507,692.
Official Action Dated Apr. 28, 2006 From the US Patent and Trademark Office Re.: U.S. Appl. No. 10/868,802.
Official Action Dated Dec. 28, 2007 From the US Patent and Trademark Office Re.: U.S. Appl. No. 10/981,522.
Official Action Dated Jul. 29, 2008 From the US Patent and Trademark Office Re.: U.S. Appl. No. 11/374,969.
Official Action Dated Nov. 29, 2006 From the US Patent and Trademark Office Re.: U.S. Appl. No. 10/981,522.
Official Action Dated Mar. 30, 2007 From the US Patent and Trademark Office Re.: U.S. Appl. No. 11/328,221.
Official Action Dated May 30, 2006 From the US Patent and Trademark Office Re.: U.S. Appl. No. 10/981,498.
Official Action Dated Nov. 30, 2006 From the US Patent and Trademark Office Re.: U.S. Appl. No. 10/981,498.
Official Action Dated Jan. 31, 2008 From the US Patent and Trademark Office Re.: U.S. Appl. No. 11/108,662.
Response Dated Jun. 16, 2009 to Official Action of Apr. 6, 2009 From the US Patent and Trademark Office Re.: U.S. Appl. No. 11/374,969.
Response Dated Nov. 23, 2009 to Official Action of Oct. 27, 2009 From the US Patent and Trademark Office Re.: U.S. Appl. No. 11/808,211.
Supplementary Partial European Search Report Dated Feb. 6, 2007 From the European Patent Office Re.: Application No. 01976586.6.
Written Opinion Dated Jun. 22, 2006 From the International Searching Authority Re.: Application No. PCT/IL05/01127.
Written Opinion Dated Jun. 24, 2008 From the International Searching Authority Re.: Application No. PCT/IL2006/000465.
Anderluh et al. "A Common Motif in Proparts of Cnidarian Toxins and Nematocyst Collagens and Its Putative Role", Biochimica et Biophysica Acta, 1476: 372-376, 2000.
Anderson et al. "A Triploblast Origin for Myxozoa?", Nature, 392(6674): 346-347, 1998.
Response Dated Dec. 30, 2009 to Office Action of Jun. 25, 2009 From the Israel Patent Office Re.: Application No. 164191.
Office Action Dated Nov. 23, 2009 From the Israeli Patent Office Re.: Application No. 155097 and Its Translation Into English.
Response Dated Feb. 22, 2010 to Office Action of Nov. 23, 2009 From the Israeli Patent Office Re.: Application No. 155097.
Office Action Dated Feb. 16, 2010 From the US Patent and Trademark Office Re.: U.S. Appl. No. 11/374,969.
Response Dated Feb. 26, 2010 to Office Action of Feb. 16, 2010 From the US Patent and Trademark Office Re.: U.S. Appl. No. 11/374,969.
Bode "The Interstitial Cell Lineage of Hydra: A Stem Cell System That Arose Early in Evolution", Journal of Cell Science, 109: 1155-1164, 1996.
Brennecke et al. "The Lack of A Stress Response in Hydra Oligactis Is Due to Reduced Hsp70 mRNA Stability", European Journal of Biochemistry, 255: 703-709, 1998.
Chapman et al. "Cytological Studies of the Nematocysts of Hydra. I. Desmonemes, Isornizas, Cnidocils, and Supporting Structures", Journal of Biophysical nad Biochemical Cytology, 5(1): 69-78, Plates 22-27, 1959.

Cikala et al. "Expression of GFP-Fusion Protein in Hydra to Investigate the Function of Genes Linked With Apoptosis", International Workshop—Evangelische Akademic, Tutzing/Germany, 2001.
Engel et al. "A Switch in Disulfide Linkage During Minicollagen Assembly in Hydra Newmatocysts", The EMBO Journal, 20(12):3063-3073, 2001.
Engel et al. "Atomic Force Microscopy: A Powerful Tool to Observe Biomolecules at Work", Trends in Cell Biology, 9:77-80, 1999.
Fernadez-Alonso et al. "DNA Vaccination by Immersion and Ultrasound to Trout Viral Heamorrhagic Septicaemia Virus", Vaccine, 19: 3067-3075, 2001.
Gerke et al. "The Spatial Distribution of Cations in Nematocytes of Hydra Vulgaris", Hydrobiologia, 216/217: 661-669, 1991.
Godknecht et al. "Discharge and Mode of Action of the Tentacular Nematocysts of Anemonia Sulcata (Antozoa: Cnidaria)", Marine Biology, 100: 83-92, 1988.
Heeger et al. "Protection of Human Skin Against Jellyfish (Cyanea Capillata) Stings", Marine Biology, 113: 669-678, 1992. Abstract.
Hidaka "Mechanism of Nematocyst Discharge and Its Cellular Control", Advances in Comparative and Environment Physiology, 15(Chap.2): 45-76, 1993.
Hidaka et al. "Effects of Calcium on the Mechanical Properties of the Capsule Wall of Isolated Nematocysts From Calliactis Polypus", Comparisons in Biochemistry and Physiology, 107A(1): 31-36, 1994.
Hiroshi et al. "Chemical Characterization of the Nematocyst Toxin From the Hawaiian Jellyfish Carybdea Alata", Symposium on the Chemistry of Natural Products, Symposium Papers, 42: 391-396, 2000. Abstract.
Holstein et al. "An Ultrahigh-Speed Analysis of Exocytosis: Nematocyst Discharge", Science, New Series, 223(4638): 830-833, 1984.
Kass-Simon et al. "The Behavioral and Developmental Physiology of Nematocysts", Canadian Journal of Zoology, 80: 1772-1794, 2002.
Kimball et al. "Efficacy of a Jellyfish Sting Inhibitor in Preventing Jellyfish Stings in Normal Volunteers", Wilderness and Environmental Medicine, 15: 102-108, 2004.
Koch et al. "Spinalin, A New Glycine- and Histidine-Rich Protein in Spines of Hydra Nematocysts", Journal of Cell Science, 111: 1545-1554, 1998.
Lohmann et al. "Silencing of Developmental Genes in Hydra", Developmental Biology, 214: 211-214, 1999.
Lotan et al. "Delivery of A Nematocyst Toxin", Nature, XP008041281, 375(6531): 456, Jun. 8, 1995.
Lotan et al. "Skin Protection Against Seabather's Eruption and Jellufish Sting", American Academy of Dermatology, p. 172-173, Poster Abstract.
Lotan et al. "Toxin Compartmentation and Delivery in the Cnidaria: The Nematocyst's Tubule as a Multiheaded Poisonous Arrow", The Journal of Experimental Zoology, 275(6): 444-451, 1996.
Lubbock "Chemical Recognition and Nematocyte Exitation in a Sea Anemone", Journal of Experimental Biology, 83: 283-292, 1979.
Lubbock et al. "Removal of Bound Calcium From Nematocyst Contents Causes Discharge", Nature, 290(5806): 500-501, 1981.
Marchini et al. "A Fast Centrifuge Method for Nematocyst Isolation From Pelagia Noctiluca Forskal (Cnidaria: Scyphozoa)", Rivista di Biologia, Biology Forum, 97: 505-516, 2004.
Marino et al. "Regulatory Volume Increase in Nematocytes Isolated From Acontia of Aiptasia Diaphana (Cnidaria, Anthozoa)", Cellular and Molecular Biology, 50: 533-542, 2004.
Miljkovic et al. "Cnidarian and Bilaterian Promoters Can Direct GFP Expression in Transfected Hydra", Development Biology, 246: 377-390, 2002.
Miljovic et al. "GFP Expression in Hydra", International Workshop—Evangelische Akademie, Tutzing/Germany, 2001. Abstract.
Murate et al. "Hydra Regeneration From Recombinant Ectodermal and Endodermal Tissue—II. Differential Stability in the Ectodeffnal and Endodermal Epithelial Organization", Journal of Cell Science, 110: 1155-1164, 1997.
Opalinska et al. "Nucleic-Acid Therapeutics: Basic Principles and Recent Applications", Nature Reviews: Drug Delivery, 1: 503-514, 2002.

Ozbek et al. "A Switch in Disulfide Linkage During Minicollagen Assembly in Hydra Nematocysts", The EMBO Journal, 20(12): 3063-3073, 2001. Abstract.
Robson "Nematocysts of Corynactis: The Activity of the Filament During Discharge", Quarterly Journal of Microscopical Science, 94(Part 3): 229-235, Sep. 1953.
Salleo et al. "Release of Free CA2+ From the Nematocysts of Aiptasia Mutabilis During the Discharge", Physiology & Zoology, 61(3): 272-279, 1988.
Sharp "RNAi and Double-Strand RNA", Genes & Development, 13: 139-141, 1999.
Siddall et al. "The Demise of a Phylum of Protists: Phylogeny of Myxozoa and Other Parasitic Cnidaria", Journal of Parasitology, 81(6): 961-967, 1995.
Smothers et al. "Molecular Evidence That the Myxozoan Protists Are Metazoans", Science, 265(5179): 1719-1721, 1994.
Stauffer et al. "Common Florida Injuries", Empulse, 8(3.2): 11-14, 2003.
Tardent "The Cnidarian Cnidocyte, A High-Tech Cellular Weaponry", BioEssays, XP00804143, 17(4): 351-362, 1995.
Tardent et al. "Morphology and Morphodynamics of the Stenotele Nematocyst of Hydra Attenuata Pall (Hydrozoa, Cnidaria)", Cell Tissue Research, 224(2): 269-290, 1982.
Thorington et al. "Control of Cnida Discharge: I. Evidence for Two Classes of Chemoreceptor", Biological Bulletin, 174: 163-171, 1988.
Verma et al. "The Achilles Heel of Gene Therapy", Genes and Resistance to Diseases, p. 148, 2000.
Wang et al. "Isolation and Characterization of a Mini-Collagen Gene Encoding a Nematocyst Capsule Protein From a Reef-Building Coral, Acropora Donei", Gene, 152(2): 195-200, 1995. Abstract.
Watson et al. "Cnidocyte Mechanoreceptors Are Tuned to the Movements of Swimming Prey by Chemoreceptors", Science, 243: 1589-1591, 1989.
Watson et al. "Receptors for N-Acetylated Sugars May Stimulate Adenylate Cyclase to Sensitize and Tune Mechanoreceptors Involved in Triggering Nematocyst Discharge", Experimental Cell Research, 198(1): 8-16, 1992.
Weber "Nematocysts (Stinging Capsules of Cnidaria) as Donnan-Potential-Dominated Osmotic Systems", European Journal of Biochemistry, 184(2): 465-476, 1989.
Weber et al. "Some Physical and Chemical Properties of Purified Nematocysts of Hydra Attenuata Pall. (Hydrozoa, Cnidaria)", Comparative Biochemistry and Physiology, 88B(3): 855-862, 1987.
Westfall et al. "Ultrastructure of the Dinoflagellate Polykrikos. I. Development of the Nematocyst-Taeniocyst Complex and Morphology of the Site for Extrusion", Journal of Cell Science, 63: 245-261, 1983.
Wittlieb et al. "Transgenic Hydra Allow In Vivo Tracking of Individual Stem Cells During Morphogenesis", PNAS, Early Edition: 1-4, 2006.
Response Dated Jun. 14, 2011 to Official Action of Apr. 11, 2011 From the US Patent and Trademark Office Re.: U.S. Appl. No. 11/374,969.
Office Action Dated Sep. 2, 2010 From the Israeli Patent Office Re.: Application No. 155097 and Its Translation Into English.
Official Action Dated Sep. 24, 2010 From the US Patent and Trademark Office Re.: U.S. Appl. No. 12/616,801.
Hyde "Skin, Hair, and Nails", The Nemours Foundation, Kidshealth, Retrieved From the Internet, p. 1-7, Apr. 21, 2001.
Office Action Dated Apr. 11, 2011 From the US Patent and Trademark Office Re.: U.S. Appl. No. 11/374,969.
Response Dated May 15, 2011 to Office Action of Feb. 27, 2011 From the Israeli Patent Office Re.: Application No. 164191.
Notice of Allowance Dated Aug. 23, 2010 From the US Patent and Trademark Office Re.: U.S. Appl. No. 11/374,969.
Response Dated Dec. 22, 2010 to Official Action of Sep. 24, 2010 From the US Patent and Trademark Office Re.: U.S. Appl. No. 12/616,801.
Response Dated Nov. 22, 2010 to Office Action of Jul. 29, 2010 From the Israel Patent Office Re. Application No. 199236.
Response Dated Nov. 22, 2010 to Office Action of Jul. 29, 2010 From the Israeli Patent Office Re.: Application No. 164191.

Response Dated Nov. 24, 2010 to Office Action of Sep. 2, 2010 From the Israeli Patent Office Re.: Application No. 155097.

Communication Pursuant to Article 94(3) EPC Dated Feb. 2, 2010 From the European Patent Office Re.: Application No. 01976586.6.

Response Dated May 17, 2010 to Communication Pursuant to Article 94(3) EPC of Feb. 2, 2010 From the European Patent Office Re.: Application No. 01976586.6.

Office Action Dated May 7, 2010 From the US Patent and Trademark Office Re.: U.S. Appl. No. 11/374,969.

Official Action Dated Jun. 18, 2010 From the US Patent and Trademark Office Re.: U.S. Appl. No. 12/616,801.

Notice of Allowance Dated Aug. 16, 2011 From the US Patent and Trademark Office Re.: U.S. Appl. No. 11/374,969.

Response Dated Jul. 14, 2010 to Official Action of Jun. 18, 2010 From the US Patent and Trademark Office Re.: U.S. Appl. No. 12/616,801.

Office Action Dated Jul. 29, 2010 From the Israel Patent Office Re. Application No. 199236 and Its Translation Into English.

Office Action Dated Jul. 29, 2010 From the Israeli Patent Office Re.: Application No. 164191 and Its Translation Into English.

Summons to Attend Oral Proceedings Pursuant to Rule 115(1) EPC Dated Feb. 16, 2012 From the European Patent Office Re.: Application No. 01976586.6.

Advisory Action Before the Filing of an Appeal Brief Dated Sep. 28, 2012 From the US Patent and Trademark Office U.S. Appl. No. 12/955,990.

Applicant-Initiated Interview Summary Dated Oct. 11, 2012 From the US Patent and Trademark Office U.S. Appl. No. 12/955,990.

Applicant-Initiated Interview Summary Dated Oct. 18, 2012 From the US Patent and Trademark Office U.S. Appl. No. 12/955,990.

Communication Under Rule 71(3) EPC Dated Sep. 21, 2012 From the European Patent Office U.S. Appl. No. 01976586.6.

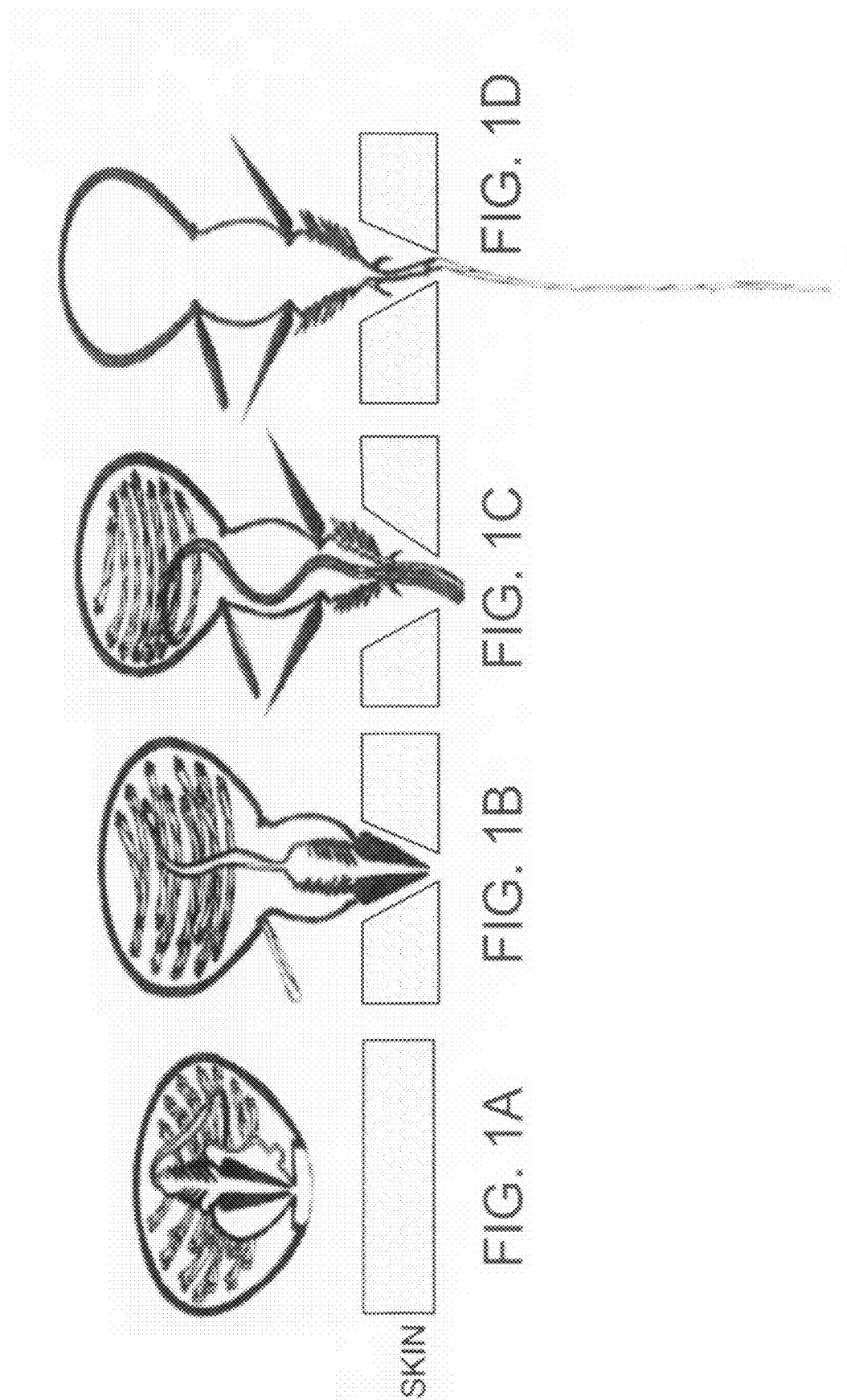

STINGING CELLS EXPRESSING AN EXOGENOUS POLYNUCLEOTIDE ENCODING A THERAPEUTIC, DIAGNOSTIC OR A COSMETIC AGENT AND METHODS COMPOSITIONS AND DEVICES UTILIZING SUCH STINGING CELLS OR CAPSULES DERIVED THEREFROM FOR DELIVERING THE THERAPEUTIC, DIAGNOSTIC OR COSMETIC AGENT INTO A TISSUE

RELATED APPLICATIONS

This application is a Divisional Application of U.S. patent application Ser. No. 10/507,692, filed on Jun. 16, 2005, which is a US National Phase of PCT Patent Application No. PCT/IL03/00241, filed on Mar. 20, 2003, which claims priority from U.S. Provisional Patent Application No. 60/367,261, filed on Mar. 26, 2002. The contents of the above Applications are incorporated herein by reference.

FIELD AND BACKGROUND OF THE INVENTION

The present invention relates to stinging cells capable of expressing an exogenous polynucleotide encoding a therapeutic, diagnostic or a cosmetic agent and to the use thereof or capsules derived therefrom in compositions, devices and methods for delivering the expressed therapeutic, diagnostic or cosmetic agent into a tissue.

Therapeutic proteinaceous agents, such as antibodies or peptide hormones are routinely used for the prevention, diagnosis, alleviation, treatment, or cure of diseases.

Biological, biochemical and/or physical barriers often limit delivery of such agents to target tissue. For example, skin and/or various organ membranes are physical barriers, which must be traversed by a topically administered agents targeted at internal tissues. Orally administered agents must be resistant to the low pH conditions and digestive enzymes present in the gastrointestinal (GI) tract.

To traverse such barriers, therapeutic agents targeted at internal tissues are often administered via a transdermal injection, using a syringe and a needle or other mechanical devices. A transdermal injection delivers such agents into the subcutaneous space thus traversing the epidermis-dermis layers.

Anatomically, the skin of a human body is subdivided into three compartments: an epidermis, a dermis and a subcutaneous layer, of which the epidermis plays a key role in blocking drug delivery via the skin (the dourest layer of the epidermis is the stratum corneum which is called also the horny layer). The epidermis is 0.1 mm or more in thickness and consists mainly of protein surrounded by lipid, thus rendering the epidermis hydrophobic.

Although the syringe and needle is an effective delivery device, it is sensitive to contamination, while use thereof is often accompanied by pain and/or bruising. In addition, the use of such a device is accompanied by risk of accidental needle injury to a health care provider.

Mechanical injection devices based on compressed gasses have been developed to overcome the above-mentioned limitations of syringe and needle devices. Such devices typically utilize compressed gas (such as, helium or carbon dioxide) to deliver medications at high velocity through a narrow aperture.

Although such devices traverse some of the limitations mentioned above, their efficiency is medication dependent, and their use can lead to pain, bruising and lacerations.

Other less common delivery methods utilize a pulsed Yag laser to perforate the stratum corneum in order to deliver agents via diffusion and enhancement of ionic compound flux across the skin by the application of an electric current. Although such methods are effective in delivering small charged molecules, a danger of skin burns accompanies their use.

Non-invasive methods, which overcome some of the limitations inherent to the invasive delivery methods described above, have also been described. Such methods utilize preparations, which include a therapeutic agent disposed within lipid vehicles (e.g., liposomes) or micelles or accompanied with skin permeation agent such that absorption of the active ingredient through the skin is enhanced. Such preparations can be directly applied to a skin region or delivered via transdermal devices such as membranes, pressure-sensitive adhesive matrices and skin patches.

In transdermal delivery, the active ingredient penetrates the skin and enters the capillary blood or the lymph circulation system, which carries the therapeutic agent to the target organ or to the tissue or has a local effect.

For several years, transdermal drug delivery systems have been employed to effectively introduce a limited number of drugs through unbroken skin. Aside from comfort and convenience, transdermal systems avoid the barriers, delivery rate control problems and potential toxicity concerns associated with traditional administration techniques, such as oral, intramuscular or intravenous delivery.

Although transdermal delivery offers an alternative to some invasive delivery methods, the efficiency thereof is affected by the physical and chemical properties of a drug and physiological or pathological parameters such as the skin hydration, temperature, location, injury, and the body metabolism.

In addition to delivery limitations, some proteinaceous drugs also suffer from limited stability making it difficult to store such drugs for extended time periods prior to use. A further limitation of conventional use of proteinaceous drugs is their limited solubility in many delivery vehicles, complicating dispersal and accurate dose delivery.

The present inventors propose a drug delivery approach utilizing stinging cells, (e.g. cnidocytes, nematocytes and the like) which express exogenous polynucleotides encoding a therapeutic, diagnostic or a cosmetic agent thereby traversing limitations associated with delivery and stability of expressed proteinaceous agents.

SUMMARY OF THE INVENTION

According to one aspect of the present invention there is provided a stinging cell or a stinging cell progenitor comprising an exogenous polynucleotide capable of expressing a therapeutic, cosmetic or diagnostic agent in the stinging cell.

According to another aspect of the present invention there is provided a pharmaceutical composition comprising, as an active ingredient, a stinging cell expressing an exogenous polynucleotide encoding a therapeutic, cosmetic or diagnostic agent and a pharmaceutically acceptable carrier.

According to yet further features in preferred embodiments of the invention described below the pharmaceutically acceptable carrier is selected from the group consisting of an aqueous solution, a gel, an oil and a semisolid formulation.

According to still another aspect of the present invention there is provided a delivery device comprising: (a) at least one stinging cell expressing an exogenous polynucleotide encoding a therapeutic, cosmetic or diagnostic agent; and (b) a support being for: (i) supporting the at least one stinging cell; and (ii) applying the at least one stinging cell to an outer surface of a tissue.

According to further features in preferred embodiments of the invention described below the device is constructed such that the at least one stinging cell is activated following application of the device to the outer surface of the tissue.

According to yet further features in preferred embodiments of the invention described below the at least one stinging cell is activated following application of the device to the outer surface of the tissue.

According to still further features in preferred embodiments of the invention described below the device comprising a mechanism for triggering the activation of the at least one stinging cell, the mechanism being selected from the group consisting of a mechanical triggering mechanism, a chemical triggering mechanism and an electrical triggering mechanism.

According to further features in preferred embodiments of the invention described below the support is selected from the group consisting of a patch, a foil, a plaster and a film.

According to a yet another aspect of the present invention there is provided a method of delivering a therapeutic or a cosmetic agent into a tissue, the method comprising the steps of: (a) transforming at least one stinging cell or stinging cell progenitor with a polynucleotide encoding a therapeutic, cosmetic or diagnostic agent to thereby generate at least one stinging cell expressing said therapeutic, cosmetic or diagnostic agent; (b) applying the at least one stinging cell expressing the therapeutic, cosmetic or diagnostic agent to an outer surface of the tissue; and (c) triggering a discharge of the at least one stinging cell to thereby deliver the therapeutic, cosmetic or diagnostic agent into the tissue.

According to further features in preferred embodiments of the invention described below the method of delivering a therapeutic or a cosmetic agent into a tissue further comprising culturing the at least one stinging cell expressing the therapeutic, cosmetic or diagnostic agent prior to step (b).

According to yet further features in preferred embodiments of the invention described below the tissue is an external or internal tissue.

According to further features in preferred embodiments of the invention described below triggering the discharge of the at least one stinging cell is performed via a mechanical triggering mechanism, a chemical triggering mechanism or an electrical triggering mechanism.

According to further features in preferred embodiments of the invention described below applying the at least one stinging cell is performed via a patch, a foil, a plaster or a film.

According to still further features in preferred embodiments of the invention described below the agent is a ribozyme and/or antisense polynucleotide.

According to further features in preferred embodiments of the invention described below the agent is a polypeptide.

According to yet further features in preferred embodiments of the invention described below the exogenous polynucleotide is further capable of expressing a molecule capable of reducing a toxicity of a toxin endogenous to the stinging cell.

According to still further features in preferred embodiments of the invention described below the molecule is capable of effectively reducing toxin expression.

According to still another aspect of the present invention there is provided a method of delivering a polypeptide into a tissue, the method comprising the steps of: (a) transforming at least one stinging cell or stinging cell progenitor with a polynucleotide designed for expressing a polypeptide being capable of self-targeting into a stinging capsule of said at least one stinging cell; (b) isolating said stinging capsule from at least one stinging cell; (c) applying said at least one stinging capsule to an outer surface of the tissue; and (d) triggering a discharge of said at least one stinging capsule to deliver said polypeptide into the tissue.

According to further features in preferred embodiments of the invention described below the polypeptide is a therapeutic, cosmetic or diagnostic agent.

According to still further features in preferred embodiments of the invention described below the at least one stinging capsule is selected from the group consisting of a cnidocyst, a nematocyst, a spirocyst and a ptychocyst.

According to further features in preferred embodiments of the invention described below the therapeutic agent is selected from the group consisting of a drug, a vaccine, a hormone, an enzyme and an antibody.

According to yet further features in preferred embodiments of the invention described below the cosmetic agent is selected from the group consisting of a cosmetic dye, an anti-wrinkling agent, an anti-acne agent, an exfoliant, a hair follicle stimulating agent and a hair follicle suppressing agent.

According to still further features in preferred embodiments of the invention described below the diagnostic agent is selected from the group consisting of a probe, a ligand, an antibody, a receptor and a receptor analog.

According to further features in preferred embodiments of the invention described below the stinging cell is selected from the group consisting of a cnidocyte, a nematocyte, a spirocyte and a ptychocyte.

According to yet further features in preferred embodiments of the invention described below the stinging cell or stinging cell progenitor is derived from an organism of a class selected from the group consisting of Anthozoa, Hydrozoa and Scyphozoa, and a phylum selected from the group consisting of Cnidaria, Dinoflagellata and Myxozoa.

According to still another aspect of the present invention there is provided an expression construct or construct system comprising a first polynucleotide sequence encoding a therapeutic, cosmetic or diagnostic agent and a second polynucleotide sequence encoding a molecule capable of at least partially downregulating activity or generation of a toxin naturally produced by a stinging cell.

According to yet further features in preferred embodiments of the invention described below the expression construct or construct system being constructed capable of transforming metazoan cells, the metazoan cells being selected from the group consisting of a cnidocyte, a nematocyte, a spirocyte and a ptychocyte.

According to further features in preferred embodiments of the invention described below the metazoan cell is derived from an organism of a class selected from the group consisting of Anthozoa, Hydrozoa and Scyphozoa, and of a phylum selected from the group consisting of Cnidaria, Dinoflagellata and Myxozoa.

According to still further features in preferred embodiments of the invention described below the first and/or second polynucleotide sequence encodes a ribozyme and/or antisense polynucleotide.

According to further features in preferred embodiments of the invention described below the agent and/or molecule is a polypeptide.

According to yet further features in preferred embodiments of the invention described below the first polynucleotide sequence encodes a therapeutic agent selected from the group consisting of a drug, a vaccine, a hormone, an enzyme and an antibody.

According to still further features in preferred embodiments of the invention described below the first polynucleotide sequence encodes a cosmetic agent selected from the group consisting of a cosmetic dye, an anti-wrinkling agent, an anti-acne agent, an exfoliant, a hair follicle stimulating agent and a hair follicle suppressing agent.

According to further features in preferred embodiments of the invention described below the first polynucleotide sequence encodes a diagnostic agent selected from the group consisting of a probe, a ligand, an antibody, a receptor and a receptor analog.

According to further features in preferred embodiments of the invention described below the expression construct or construct system further comprises a third polynucleotide sequence being translationally fused with the first polynucleotide and encoding a signal peptide for transport into a capsule of the stinging cell.

The present invention successfully addresses the shortcomings of the presently known configurations by providing a natural delivery device for delivering therapeutic, cosmetic and diagnostic agents. By exploiting one of the most efficient systems that exist in biology it is possible to use stinging cells and/or capsules as delivery vehicles for drugs, vaccines, antibodies, nucleic acids and other agents.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-d illustrate the structure and release mechanism of a cnidocyst.

Figure 1E:
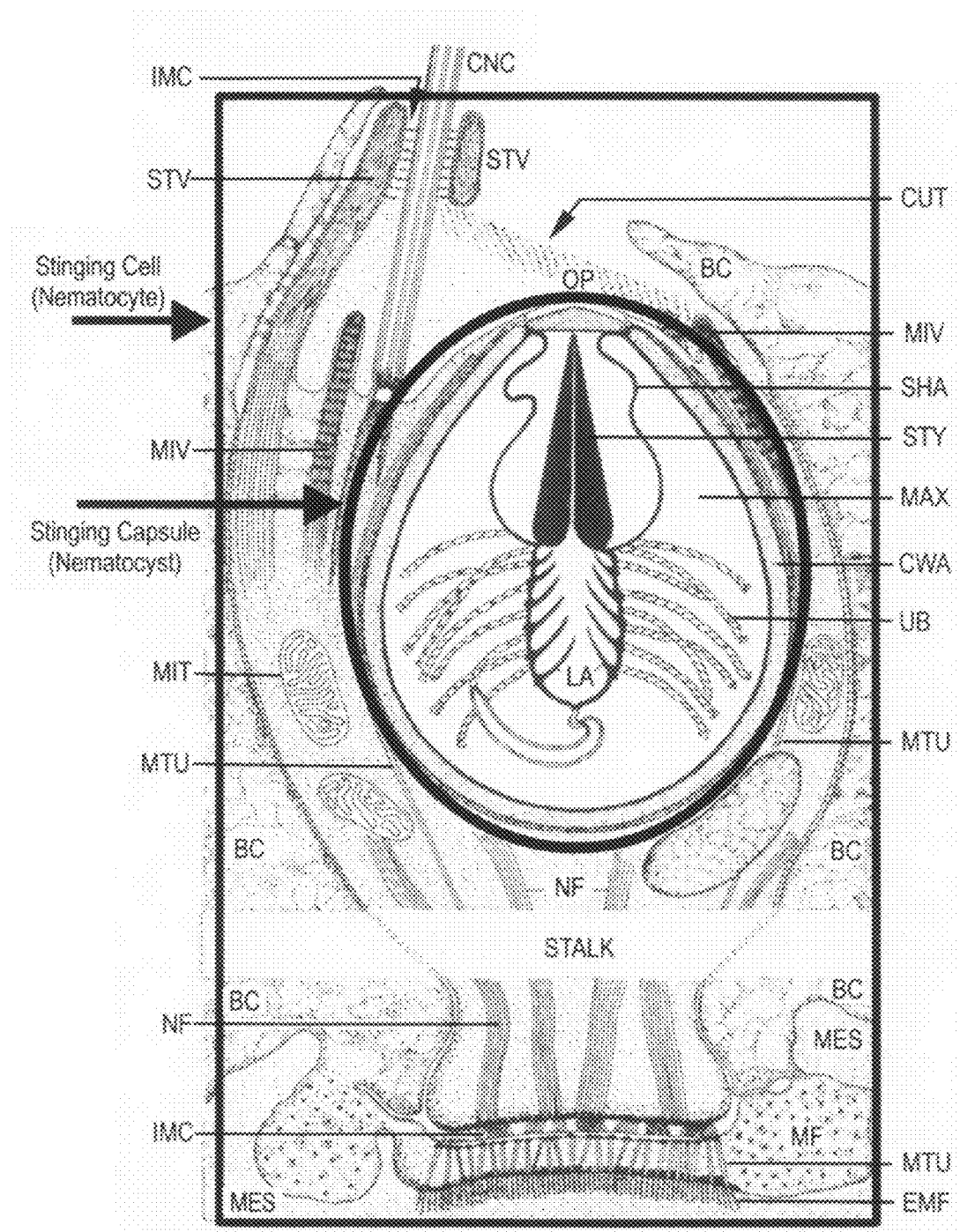

FIG. 1e schematically illustrates the structure of a stinging cell illustrating the stinging capsule sequestered thereby (Adapted from Tardent 1995).

Figure 2:
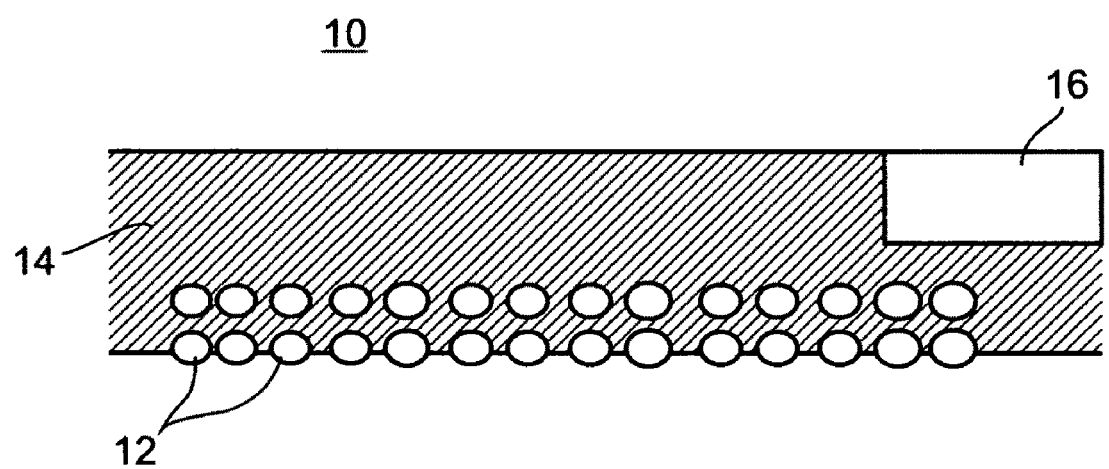

FIG. 2 is a schematic illustration of a delivery device according to the teachings of the present invention.

Figure 3:
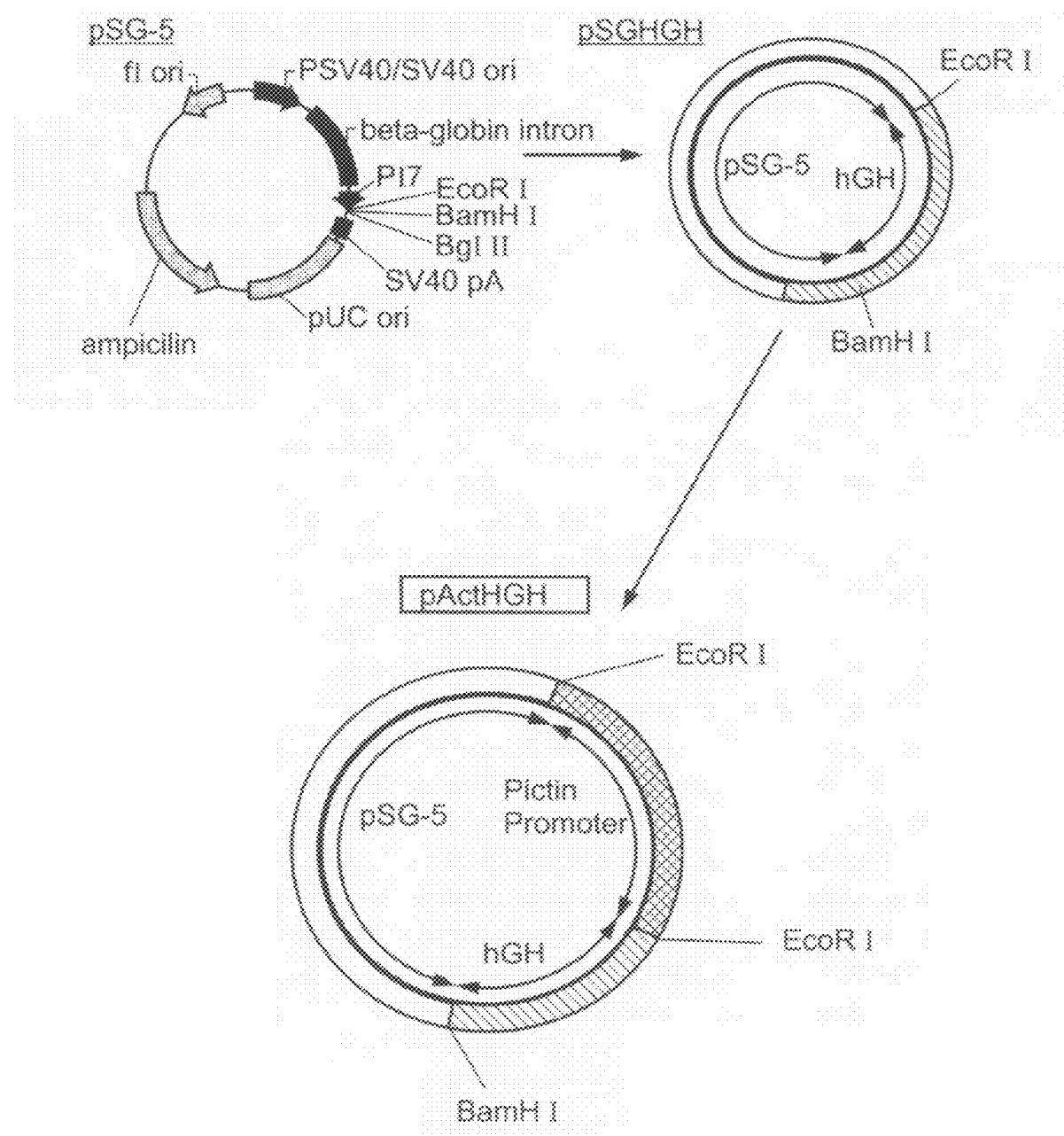

FIG. 3 is a schematic depicting the construction of expression vector pActHGH.

Figure 4:
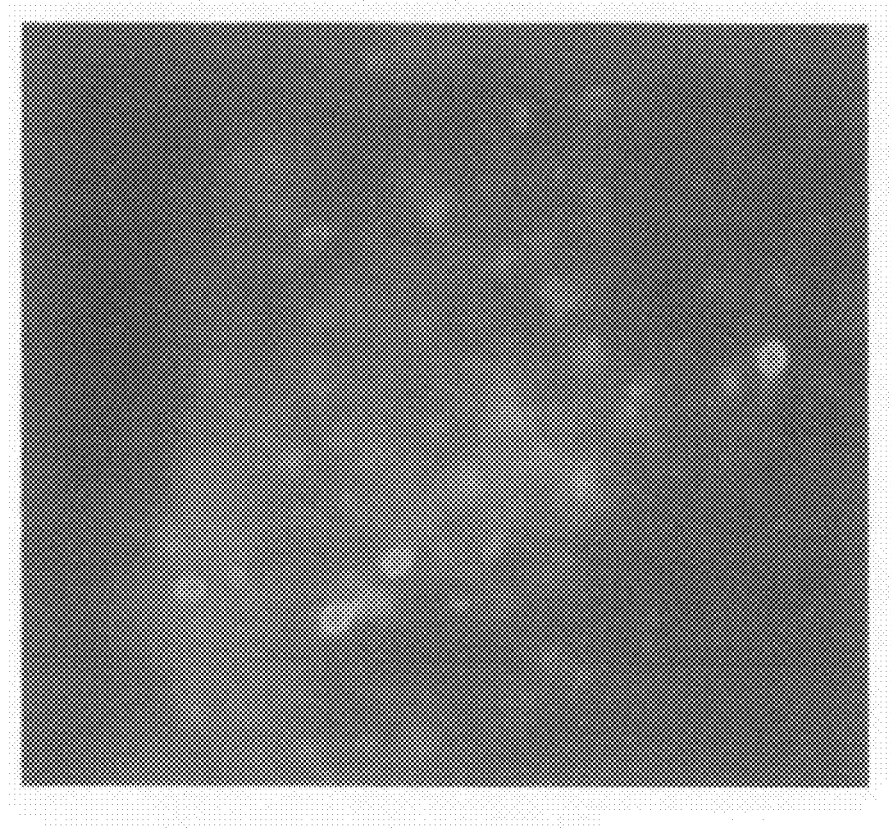

FIG. 4 is a fluorescent image depicting hydra capsules expressing GFP 48 hours following electroporation with an expression construct encoding EGFP linked to a signal peptide for transport into a capsule.

DESCRIPTION OF THE PREFERRED EMBODIMENTS

The present invention is of compositions, devices and methods utilizing stinging cells transformed to express a therapeutic, cosmetic or diagnostic agent, which stinging cells can be used, for example, for transdermal/intradermal, transmucosal or transcuticular delivery of such a therapeutic, cosmetic or diagnostic agent. Specifically, the present invention relates to the design and use of constructs for transforming metazoan cells to express exogenous polynucleotide sequences encoding such a therapeutic, cosmetic or diagnostic agent, and the utilization of such transformed metazoan stinging cells for delivery of such agent.

The principles and operation of the present invention may be better understood with reference to the drawings and accompanying descriptions.

Before explaining at least one embodiment of the invention in detail, it is to be understood that the invention is not limited in its application to the details of components and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Cnidaria (hydras, sea anemones, jellyfish and corals) are aquatic animals, which possess a variety of compounds which are stored and delivered via specialized capsules (cnidocysts, FIGS. 1a-d), which form a part of specialized cells termed stinging cells (cnidocytes, nematocytes, ptychocytes and the like, FIG. 1e). The stinging capsules act as microscopic syringes and serve as a prey or defense mechanism. The Cnidaria family which encompasses 10,000 known species, includes sedentary single or colonial polyps and pelagic jellyfish. In some of these species, cnidocytes account for more than 45% of the cells present (Tardent 1995).

As shown in FIGS. 1a-e, the cnidocyst is a hardened dense capsule, filled with liquid containing a highly folded inverted tubule which sometimes features specialized structures such as shafts, barbs, spines, and/or stylets. In nature, the cnidocyst discharges and releases its tubule (FIG. 1d) into tissue following physical and chemical triggering.

Discharge is initiated by a rapid osmotic influx of water which generates an internal hydrostatic (liquid) pressure of 150 atmospheres forcing capsule rupture and ejection of the tubule (Holstein and Tardent 1984). During ejection, the long coiled and twisted tubule is everted and its length increases by 95 percent. Accelerating at 40,000 g, the tubule untwists to generate a torque force, which rotates the tubule several times around its axis. These mechanical processes generate a powerful driving force, which enables efficient delivery of the compounds, the toxins and enzymes stored within the capsule (Lotan et al. 1995, 1996; Tardent 1995). This process, which occurs within microseconds, is among the most rapid exocytosis events in biology (Holstein and Tardent 1984).

There are at least three dozen known types of cnidocysts (also termed cnidae) including more than 30 varieties of nematocysts found in most Cnidaria and spirocysts, and ptychocysts found mainly in the Cnidaria class Anthozoa (Mariscal 1974).

As is further described herein, the present invention exploits the unique delivery mechanism of stinging cells and their capability to support expression of exogenous polynucleotides for delivering proteinaceous therapeutic, diagnostic or cosmetic agents into tissues of a metazoan organism, such as, for example, a mammal.

By utilizing stinging cells for expressing and delivering a proteinaceous agent of choice, the present invention enables easy, efficient and painless delivery of a therapeutic, diagnostic or cosmetic agents into, for example, mammalian tissues such as for example dermal tissues.

The use of such stinging cells or capsules derived therefrom for delivery enables an accurate and localized delivery of precise dosages while being devoid of the pain and discomfort associated with other invasive delivery methods. In addition, by utilizing stinging cells or capsules for delivery, the present invention enables precise control over the depth of penetration and as such the tissue region of delivery. Tubules are capable of penetrating through tissue to a depth of up to 800 microns, depending on the tissue and stinging cell types from which they are discharged. As such, different stinging cell types can be utilized for delivery into different tissue regions or depths.

Furthermore, by expressing the therapeutic, cosmetic or diagnostic agent within the delivery device (stinging cell), the present invention overcomes problems associated with stability/solubility of such agents.

Thus, according to one aspect of the present invention there is provided a stinging cell or stinging cell progenitor which expresses an exogenous polynucleotide encoding a therapeutic, cosmetic or diagnostic agent.

Preferably, the exogenous polynucleotide encoding a therapeutic, cosmetic or diagnostic agent forms a part of an expression construct designed and configured for expressing the exogenous polynucleotide within the stinging cell. Expression constructs suitable for use with the present invention, methods of transforming stinging cells with such constructs and methods of culturing transformed stinging cells are described in detail hereinbelow.

As used herein, the term "expressed" when used in context with the exogenous polynucleotide encoding a therapeutic, cosmetic or diagnostic agent refers to generation of a polynucleotide (transcript) or a polypeptide product.

Examples of therapeutic agents which can be expressed within stinging cells include but are not limited to polypeptides such as peptide hormones, antibodies or antibody fragments (e.g., Fab), enzymes and structural proteins or antisense/ribozyme transcripts which can be directed at specific target sequences (e.g., transcripts of tumor associated genes) to thereby downregulate activity thereof and exert a therapeutic effect. Similarly, protective protein antigens for vaccination (see, for example, Babiuk S et al J Control Release 2000; 66:199-214) and enzymes such as fibrinolysin for treatment of ischemic damage (U.S. Pat. No. 5,078,995 to Hunter et al) may expressed in the stinging cells for transdermal or transcutaneous delivery. The therapeutic agent can also be a prodrug, which is activatable prior to, during, or following discharge of the stinging cell. As used herein in the specification and in the claims section which follows, the term "prodrug" refers to an agent which is inactive but which is convertible into an active form via enzymatic, chemical or physical activators.

A prodrug (for example an enzyme) can be activated just prior to stinging cell discharge by providing an activator compound (for example an ion), which can be diffused or pumped (during discharge) into the cell or capsule. Alternatively, specific enzymes, molecules or pH conditions present in the target tissues, can activate the prodrug.

Examples of cosmetic agents which can be expressed within stinging cells include but are not limited to proteases, such as annain, collagenase, Vibriolysin, for burn debridement, exfoliation, acne and abnormal skin conditions (see, for example, U.S. Pat. Nos. 5,976,556 and 5,958,406 to Norton, et al and deFaire, et al, respectively), TGF-beta RII agonists and antagonists for stimulation or suppression of hair growth (Foitzik K et al FASEB J 2000; 14:752-60) and alpha-interferon for care of aged or damaged skin (U.S. Pat. No. 6,325, 987 to Marini) and cosmetically used toxins such as the Botulinum toxin (GenBank Accession number AF464912).

Examples of diagnostic agents which can be expressed within stinging cells include but are not limited to polynucleotide probes, specific ligands, antibodies, receptor, receptor analogs (such as antibodies, ligands and receptors for detection of specific markers of cancer and infection) and the like. Radioactive, spin-tagged and other detectable ligands can be expressed within the stinging cells cultured in medium containing a tagged nucleic or amino acids.

The stinging cell according to the teachings of the present invention can be an isolated stinging cell or alternatively it can form a part of a stinging organ (e.g., tentacle). In any case, the stinging cell is derived from an organism of the phylum Cnidaria, Myxozoa, or Dinoflagellata preferably from an organism of the class Anthozoa, Hydrozoa or Scyphozoa.

More specifically, the stinging cell utilized by the present invention can be derived from, for example, subclasses Hexacorallia or Octocorallia of the class Anthozoa, (mostly sea anemone and corals), subclasses Siponophora or Hydroida of the class Hydrozoa, or from subclasses Rhisostomeae or Semastomeae of the class Scyphozoa.

Stinging cells from such organisms include toxins, which are non-toxic to humans, and other mammals. As such, stinging cells isolated therefrom are ideally suited for safe and efficient delivery of expressed agent into mammalian tissue.

It will be appreciated that the use of stinging cells from organisms which sequester toxins that are not fatal but cause only minor irritations to, for example, mammals, is also envisioned by the present invention.

In addition, stinging cells from other sources can also be utilized by the present invention provided inactivation of the endogenous toxin is effected prior to use.

Such inactivation can be effected via one of several methods, including but not limited to, temperature or chemical denaturation, enzymatic inactivation, ligand inactivation (e.g., Fab fragment of an antibody).

Inactivation of such toxins can also be effected by transforming the stinging cell with polynucleotide sequences encoding a polynucleotide capable of inhibiting toxin synthesis (e.g. antisense or ribozyme), or encoding an enzyme or an antibody capable of inactivating the endogenous toxin protein, such as has been described for Chrysaora venom (Radwan FF et al Toxicon 2000; 38:1581-91, and Olson C E et al Toxicon 1985; 23:307-16) and tick neurotoxin (Masina S and Brody K W Int J Parasit 1999; 29:535-41).

The polynucleotide sequence encoding such a polynucleotide or enzyme can be introduced into the stinging cell along with the exogenous polynucleotide encoding a therapeutic, cosmetic or diagnostic agent described above thereby greatly simplifying the process of stinging cell preparation. Preferably, such co-transformation is effected using a single expression construct expressing both polynucleotides. Further detail of expression constructs and methodology is provided hereinbelow.

The stinging cell of the present invention can be isolated from a cell extract prepared from organs or parts of an organism, which contain the stinging cells (for example a whole hydra or tentacles). Alternatively stinging cell progenitors, such as stem cells, which give rise to cnidocytes or cnidocysts, can be isolated and cultured or utilized directly.

Preferably, the exogenous polypeptide expressed by the stinging cell is designed to be self targeting into the capsule such that following capsular accumulation of the expression product, the capsule can be isolated from the stinging cell and used in the therapeutic, diagnostic or cosmetic applications described herein.

The following section describes in detail expression constructs suitable for use with the present invention, methods which can be used to transiently or stably transform isolated stinging cells or whole organisms with such expression construct and methods suitable for inducing/sustaining expression of the therapeutic, cosmetic or diagnostic agent within the transformed stinging cells.

Expression of exogenous polynucleotides in stinging cells, accumulation of an expression product therein and delivery of the accumulated expression product from the stinging capsule into tissue depends upon:

(i) construction of expression constructs suitable for transient (exchromosomal) or stable (chromosomal integration) transformation of stinging cells, (in particular, selection of suitable promoter sequences);

(ii) selection of suitable transformation methods; and
(iii) selection of suitable culturing conditions.

Expression Construct

To enable expression of a therapeutic, cosmetic or diagnostic agent, in stinging cells, the expression construct of the present invention must include regulatory sequences which are capable of directing expression of polynucleotide sequence encoding the therapeutic, cosmetic or diagnostic agent in stinging cells.

The regulatory sequence utilized can be either a constitutive or inducible promoter. Enhancers that may be required to obtain necessary transcription levels can optionally be included. Enhancers are generally any cis acting nontranslated DNA sequence which change the basal transcription level established by the promoter. Vectors may also include such expression control sequences as origin of replication, a promoter, and necessary processing information sites, such as ribosome binding sites, RNA splice sites, polyadenylation sites and transcriptional terminator sequences. The expression vehicle can also include a selection gene, for example, kanamycin (antibiotic) resistance.

An expression vector for expressing exogenous polynucleotides in Hydra has been described by Brennecke (Brennecke T et al Eur J Bioch 1998; 225:703-9). Firefly luciferase coding sequence was fused to heat shock protein (HSP 70) regulatory sequences derived from Hydra magnipapillata, and introduced into Hydra oligactis. The heterologous coding sequence was accurately expressed (luminescence) in a heat inducible manner, indicating successful function of the chimeric metazoan-arthropod construct.

Thus, the expression construct of the present invention can utilize such regulatory sequences for directing expression of any exogenous polynucleotide within stinging cells.

In addition, regulatory sequences isolated from cnidarian genomes or genomes of related organisms can also be used by the present invention [see, for example, Miljkovic et al. Developmental Biology 246, 377-390 (2002)].

Molecular studies of cnidarian genes have revealed substantial identity with their mammalian homologues, indicating extensive conservation of coding and regulatory signals (see, for example, Yon L, et al Dev Genes Evol 2000; 210: 507-11; Broun M et al Development 1999; 126:5245-54 and Jeziorski M C et al Receptors Channels 1999; 6:375-86). Indeed, many cnidarian genes have been cloned and accurately expressed in chordate cells, such as the green fluorescent protein GFP, the high voltage $Ca^{++}$ channel subunit from Cyanea cappilata CyCa beta (Jeziorski M C et al Receptors Channels 1999; 6:375-86) and the ancestral coral cyclooxygenase from Gersemia fruticosa (Koljak R et al J Biol Chem 2001; 276:7033-40).

Furthermore, promoter sequences that have been successfully used in expression of foreign genes in diverse species may also be used by the constructs of the present invention. For example, general, well defined promoter sequences of chicken β-actin and C. elegans ribosomal genes have successfully directed expression of GFP in hydra (Miljkovic and Galliot 2001 International workshop on Hydra and the evolution of metazoan development). Critical 5' and 3' control elements from Cnidaria can be identified by cloning PCR-amplified portions of 5' and 3' flanking sequences of known metazoan genes into reporter expression vectors, and measuring their effect on reporter expression following transformation of the metazoan hosts (see U.S. Pat. No. 5,891,634 to Petri Jr, et al for strategy of control element identification).

In addition to regulatory and coding sequences, the expression construct of the present invention can also include sequences functional in bacteria which can serve as a replication host. Such sequences can include a bacterial origin of replication and an antibiotic resistance gene.

The expression construct of the present invention can also include sequences which facilitate integration of the expression cassette into a genome of the host cell. It will be appreciated that since organisms of the Cnidaria class are capable of being somatically cloned, stable (chromosomal) transformation can be used to generate whole organisms expressing the exogenous polynucleotide from single transformed cells. Cotransfection with an expressible selectable marker, such as the G418 resistance gene "neo", provides means for selection of organisms with high likelihood of stable construct integration. Such whole organisms, selected for strong expression and stability of the transfected sequences can be used as a source for modified stinging cells and stinging cell progenitors.

The expression construct of the present invention may also include additional coding sequences which can code for an RNA transcript (antisense/ribozyme) or a polypeptide capable of inactivating a toxin stored by stinging cells.

Since the expression product of the exogenous polynucleotide is ultimately delivered by the stinging capsule, it may be beneficial to direct the expressed product into the capsule.

Thus, in one preferred embodiment the stinging cell or stinging cell progenitor is transformed with a polynucleotide designed for expressing a polypeptide being capable of self-targeting into a stinging capsule. The therapeutic, diagnostic or cosmetic polypeptide agents expressed in the stinging cells of the present invention can thus be transported into the capsule and packaged for extrusion.

Transport of expressed polypeptides is achieved via a leader or signal peptide.

Signal peptides play an important role in protein transport and sorting of expressed proteins to different cell compartments. Signal peptides control the entry of virtually all proteins to the secretory pathway, both in eukaryotes and prokaryotes (Gierasch, 1989; von Heijne, 1990; Rapoport, 1992). The signal peptides take part in an array of protein-protein and protein-lipid interactions. The result is initiation of protein translocation through a proteinaceous channel, in the endoplasmic reticulum (ER) of eukaryotic cells. Once the protein targets to a location, the signal peptide is cleaved by a signal peptidase (von Heijne, 1998).

Nematocysts are self-assembled in a post Golgi vacuole (Engel et al, 2001; Holstein, 1981). Thus, proteins that are expressed within the capsule posses the appropriate signal peptide for intra-capsule transport. As a result, signal peptide sequences derived from such proteins can be utilized by the present invention to transport heterologous sequences into the capsule.

In addition, other signal peptides may also be functional in capsule transport and thus can be utilized with the present invention.

Signal peptides have varying lengths. The average length in eukaryotes is 22.6 amino acid. There is no consensus sequence but almost all signal peptides possess a common structure: a short, positively charged amino region (n-region); a central hydrophobic region (h-region); and a more polar region (c-region) containing the site that is cleaved by the signal peptidase (von Heijne, 1997).

The SignalP V2.0 Web application (Center for Biological Sequence Analysis, University of Denmark DTU web site) was used to assess the intra capsule transport capability of specific sequences. This application utilizes neural networks (NN) and hidden Markov models (HMM) which were trained on eukaryote sequences (von Heijne, 1997; Krogh, 1998).

Table 1 which follows provides several examples of signal peptides which can be utilized by the present invention. Analysis and comparison of the amino acid sequences of these signal peptides is provided in Table 2.

TABLE 1

Signal peptides

| Name | Length (in Amino acids) | Nucleotide coordinates/GenBank Accession number | Reference |
|---|---|---|---|
| AeNa signal peptide | 20 | 68-124 AF130344 | B.B.A 1476 (2), 372-376 2000 |
| AeNa signal peptide | 29 | 68-151 AF130344 | B.B.A 1476 (2), 372-376 2000 |
| Hetractis magnifica K channel toxin | 23 | 757-873 AF020047 | FEBS Lett. 418 (1-2), 183-188 (1997) |
| Hydra N-COL 1 mini collagen | 16 | 14-61 X61045 | J. Cell Biol. 115 (4), 1159-11691 (1991) |
| Apis mellifera phospholipase A2 | 20 | 135-188 AF438408 | J Biol Chem 2002; 277(43): 40839-43 |
| Adamsia carciniopados phospholipase A2 signal peptide | 20 | 23-79 AF347072 | Comp Biochem Physiol B Biochem Mol Biol 2002 132 (3): 571-578 |
| Human Erythropoietin; glycoprotein hormone signal peptide | 28 | 182-262 X02157 | Nature 313 (6005), 806-810 (1985) |
| Human coagulation factor VII signal peptide | 21 | 52-165 NM_019616 | Proc. Natl. Acad. Sci. U.S.A. 83 (8), 2412-2416 (1986) |
| Human Insulin signal peptide | 24 | 2424-2495 J00265 | Nature 284 (5751), 26-32 (1980) |
| Human secretin signal peptide | 18 | 31-84 NM_021920 | Cytogenet. Cell Genet. 90 (1-2), 47-52 (2000) |
| Human growth hormone signal peptide | 26 | 5225-5234; 5495-5562 J03071 | Genomic 4 (4), 479-497 (1989) |

TABLE 2

Signal peptides analysis

| SEQ ID NO: | Signal peptide origin | Amino Acids | Signal Probability | Max cleavage site probability |
|---|---|---|---|---|
| 7 | Actinia equina sodium Channel Inhibitor precursor | MANRLMIVFAAVFLALASA | 1 | 0.955 |
| 8 | Actinia equina sodium Channel Inhibitor precursor* | MANRLMIVFAAVFLALASADEDVDIAKR | 1 | 0.958 |
| 9 | Heteractis magnificia K channel Toxin precursor | MAKSQMIAAVLLIAFCLCVVVTA | 0.975 | 0.471 |
| 10 | Hydra N-COL 1 mini collagen | MAMRLVLACLVLGVAA | 1 | 0.826 |
| 11 | Apis mellifera phospholipase A2 | MAQVVLLGSLFLLLLSTSHG | 1 | 0.956 |
| 12 | Adamsia carciniopados Phospholipase A2 | MAQLYTYFFTFSLVLILALA | 0.943 | 0.689 |
| 13 | Erythropoietin (Human) | MAGVHECPAWLWLLLSLLSLPLGLPVLG! | 0.999 | 0.925 |
| 14 | Coagulation factor VII (Human) | MAVSQALRLLCLLLGLQGCLA | 0.999 | 0.948 |
| 15 | Insulin (Human) | MALWMRLLPLLALLALWGPDPAAA! | 1 | 0.893 |
| 16 | Secretin (Human) | MAPRPLLLLLLLLGGSAA | 1 | 0.838 |
| 17 | Groth hormone 1 | MATGSRTSLLLAFGLLCLPWLQEGSA | 1 | 0.921 |

Signal peptide probability value given according to HMM prediction (euk models)
Max cleavage site probability value given according to HMM prediction (euk models)
A-The amino acid alanine was added to the published sequence.
*see reference Biochim Biophys Acta 2000 1476 (2): 372-6

■ cleavage site according to HMM and NN prediction (euk models)
bold-n-region, positively charged ▯-h-region, hydrophobic ▨-c-region, neutral but polar Additional signal peptides which can be utilized by the present invention include the 17 amino acid N-terminal signal peptide of the hydra cnidocyte protein spinalin (Koch A W et al J Cell Sci 1998; 111:1545-54, GenBank Accession No AF043907) and the 9 amino acid signals identified in hydra (Anderluh, et al Biochem Biophys Acta 2000; 1476:372-6).

Thus, the expressible polynucleotide of the present invention may contain additional elements for efficient compartmentalization and packaging of the foreign polyp, such as polynucleotide sequences encoding signal peptides placed downstream of the polypeptide's coding sequence. Likewise, the expressed polypeptide may be targeted to a specific location within the cell by constructing a chimeric recombinant expressible polynucleotide containing truncated native coding sequences fused with the foreign polynucleotide sequences. By choosing native proteins that demonstrate a unique localization within the cnidocyst, such as phospholipase A2 from Rhopilema nomadica nematocysts (Lotan et al 1996) the foreign protein agents of the present invention may be compartmentalized upon synthesis.

The polynucleotide sequence expressed from the construct of the present invention can encode any functional agent, including, for example, an antibody which can be used as a therapeutic or diagnostic agent.

The term "antibody" as used in this invention includes intact molecules as well as functional fragments thereof, such as Fab, F(ab')$_2$, and Fv that are capable of binding to antigens.

Antibody fragments such as a single polypeptide chain with a linker peptide bridging the two V domains can be expressed in, and subsequently delivered by, stinging cells.

The polynucleotide sequence encoding the bridged antibody fragment is inserted into the expression construct downstream of the promoter region, and the construct is introduced into the stinging cell as described hereinbelow. The transformed host cell is then cultured under suitable conditions (further detailed below) thereby synthesizing a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide comprising a single complementarity-determining region (CDR) or CDR peptides ("minimal recognition units"). CDR coding sequences are prepared, for example, by using the polymerase chain reaction to synthesize the variable region from RNA of antibody-producing cells. See, for example, Larrick and Fry, Methods, 2: 106-10, 1991.

Human antibodies can be made by introduction of whole human immunoglobulin loci into transgenic animals, e.g., metazoans. This approach is described, for example, in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13, 65-93 (1995).

Another example of an agent which can be expressed in the modified stinging cells of the present invention is an antisense molecule. Design of an antisense molecule which can be used to efficiently inhibit expression of a specific target sequence must take into account sequence elements which enable the oligonucleotide to specifically bind the designated mRNA within cells in a way which inhibits translation thereof.

Algorithms for identifying those sequences with the highest predicted binding affinity for their target mRNA based on a thermodynamic cycle that accounts for the energetics of structural alterations in both the target mRNA and the oligonucleotide are widely available [see, for example, Walton et al. (1999) Biotechnol Bioeng 65(1): 1-9].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries. In addition, several approaches for designing and predicting efficiency of specific oligonucleotides using an in vitro system were also published (Matveeva et al. (1998) *Nature Biotechnology* 16, 1374-1375).

Several clinical trials have demonstrated safety, feasibility and activity of antisense oligonucleotides. For example, antisense oligonucleotides suitable for the treatment of cancer have been successfully used (Holmund et al. (1999) Curr Opin Mol Ther 1(3):372-85), while treatment of hematological malignancies via antisense oligonucleotides targeting c-myb gene, p53 and Bcl-2 had entered clinical trials and had been shown to be tolerated by patients [Gerwitz (1999) Curr Opin Mol Ther 1(3):297-306].

More recently, antisense-mediated suppression of human heparanase gene expression has been reported to inhibit pleural dissemination of human cancer cells in a mouse model [Uno et al. (2001) Cancer Res 61(20:7855-60].

Thus, the current consensus is that recent developments in the field of antisense technology which, as described above, have led to the generation of highly accurate antisense design algorithms enabling an ordinarily skilled artisan to design and implement antisense approaches suitable for downregulating expression of known sequences without having to resort to undue trial and error experimentation.

Another mechanism of down regulating toxin expression at the transcript level is RNA interference (RNAi), an approach which utilizes small interfering dsRNA (siRNA) molecules that are homologous to the target mRNA and lead to its degradation [Carthew, 2001, Curr Opin Cell Biol 13(2):244-8]. RNAi is an evolutionarily conserved surveillance mechanism that responds to double-stranded RNA by sequence-specific silencing of homologous genes (Fire et al., 1998, Nature 391, 806-811; Zamore et al., 2000, Cell 101, 25-33). RNAi is initiated by the dsRNA-specific endonuclease dicer, which promotes cleavage of long dsRNA into double-stranded fragments between 21 and 25 nucleotides long, termed small interfering RNA (siRNAs) (Zamore et al., 2000, Cell 101, 25-33; Elbashir et al., 2001, Genes Dev. 15, 188-200; Hammond et al., 2000, Nature 404, 293-296; Bernstein et al., 2001, Nature 409, 363-366). siRNA are incorporated into a protein complex that recognizes and cleaves target mRNAs (Nykanen et al., 2001, Cell 107, 309-321).

RNAi has been increasingly used for the sequence-specific inhibition of gene expression. The possibility of interfering with any specific target RNA has rendered RNAi a valuable tool in both basic research and therapeutic applications. RNAi was first used for gene silencing in nematodes (Fire et al., 1998, Nature 391, 806-811).

Recent scientific publications have validated the efficacy of such short double stranded RNA molecules in inhibiting target mRNA expression and thus have clearly demonstrated the inhibitory potential of such molecules. For example, RNAi has been utilized to inhibit expression of hepatitis C (McCaffrey et al., 2002, Nature 418, 38-39), HIV-1 (Jacque et al., 2002, Nature 418, 435-438), cervical cancer cells (Jiang and Milner 2002, Oncogene 21, 6041-8) and leukemic cells (Wilda et al., 2002, Oncogene 21, 5716-24).

The siRNA used by the present invention can be transcribed in vitro from plasmids and administered into the stinging cells. Transcripts that include two self-complementary siRNAs annealed to form a loop region can be further processed by single-stranded ribonucleases and/or other proteins into a functional duplex siRNA molecule (Leirdal and Sioud, 2002, Biochem Biophys Res Commun 295, 744-8). siRNA can also be prepared from dsRNA by *Escherichia Coli* RNase III cleavage into endoribonuclease-prepared siRNA (esiRNA). Alternatively, siRNA can be directly expressed within stinging cells using expression using expression vectors engineered to express small hairpin RNAs (shRNAs), which are processed in vivo into siRNA molecules capable of carrying out gene-specific silencing [Brummelkamp, T. R., et al., (2002) Science 296: 550-53; Paddison, P. J., et al., (2002) Genes Dev. 16:948-58; Paul et al. (2002) Nature Biotech. 20: 505-08, Yu, J. Y et al., (2002) Proc. Natl. Acad. Sci. USA 99: 6047-52].

Transformation Methodology

Expression constructs can be introduced into cells or tissues by any one of a variety of transformation methods used in the art. Such methods can be found generally described in Sambrook et al., Molecular Cloning: A Laboratory Manual, Cold Springs Harbor Laboratory, New York 1989, 1992), in Ausubel et al., Current Protocols in Molecular Biology, John Wiley and Sons, Baltimore, Md. 1989), Chang et al., Somatic Gene Therapy, CRC Press, Ann Arbor, Mich. 1995), Vega et al., Gene Targeting, CRC Press, Ann Arbor Mich. (995), Vectors: A Survey of Molecular Cloning Vectors and Their Uses, Butterworths, Boston Mass. 1988) and Gilboa et al. (Biotechniques 4 (6): 504-512, 1986) and include, for example, stable or transient transfection, lipofection, virus infection, particle gun bombardment (see, for example, David R E et al PNAS 1999; 96:8687-92 or Bottger et al. Dev Genes Evol (2002) 212:302-305), glass fibers or silicon carbide whisker transformation of cell cultures (see, for example U.S. Pat. No. 5,464,765), ultrasound (see Fernandez et al Vaccine 2001; 19:3067-3075), vacuum infiltration, and electroporation (see, for example, Bosch et al. Differentiation (2002) 70:140-147 and U.S. Pat. No. 5,891,634 to Petri Jr et al).

It should be noted that when mechanical transformation methods are utilized (e.g., microinjection, biolistic bombardment and glass fibers or silicon carbide whisker transformation), care must be taken not to damage the stinging cells or activate discharge of the stinging capsule.

Since the activation of stinging capsules is regulated by chemical and mechanical receptors, mechanical force of the transformation methodology alone is not sufficient to activate the cnidocysts. However, since mechanical transformation of the stinging cells of the present invention may damage the tissue, regeneration and polyp recovery of a few days after transformation should be provided. For example, Brennecke et al incubated the hydra polyps for 4 days at 18° C. following their transformation by electroporation with the construct pAVLUC.

Viruses that normally infect metazoan species may also be employed to introduce the expressible polynucleotides into the stinging cells. Metazoan species are susceptible to infection by viruses of the poxvirus and iridovirus family, similar to the vaccinia virus that has been widely used in transformation of mammalian cells. Viral promoters are often strong promoters, providing superior efficiency of transcription of downstream foreign coding sequences. Further, the viral DNA or RNA can replicate within the infected cell, amplifying the expressible polynucleotide sequences and increasing yield of the therapeutic, diagnostic or cosmetic agents for delivery.

Introduction of nucleic acids via viral infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny.

A specific example of DNA viral vector introducing and expressing recombination sequences is the adenovirus-derived vector Adenop53TK. This vector expresses a herpes virus thymidine kinase (TK) gene for either positive or negative selection and an expression cassette for desired recombinant sequences. This vector can be used to infect cells that have an adenovirus receptor.

The biological material that may be transformed may vary: transformation may be performed on a variety of metazoan species or on different parts of the same species. For example, whole hydra polyps may be used (see Cikala et al 2001: International Workshop on Hydra and The Evolution of Metazoan Development, and Miljkovic and Galliot 2001: International Workshop on Hydra and The Evolution of Metazoan Development), the isolated budding region of the polyp may be used after dissection, the isolated endoderm and ectoderm may be used, cell suspensions of hydra cells which can form fresh hydra from aggregates may be used, and the fertilized egg itself may be used after temperature shock.

Likewise, integration of the foreign DNA into the metazoan genome may ensure even greater stability and efficient delivery of the expressible gene products. Such integration may be enhanced by the inclusion of recognized insertion elements, such as the inverted repeats found in eukaryotic genomes, flanking the expressible sequences of the agents of the present invention.

In addition, since it is hypothesized that protein sorting into the capsule occur before the capsule is "sealed", preferably transformation is effected at a stage prior to capsule maturation (Engel et al., EMBO 20:3063-73 2001).

Culturing Conditions

Hydra, and Hydra cells are cultured according to methods well known in the art (for exhaustive discussion of methods see Hydra: Research Methods; H. M. Lenoff, 1983, Plenum Press). Hydra culture medium contains 1 mM $CaCl_2$, 1 mM Tris-HCl, pH 7.6, 1 mM $NaHCO_3$, 0.1 mM KCl and 0.1 mM $MgCl_2$. Cultures of Hydra are maintained in glass or plastic containers. The Hydra are fed freshly hatched Artemia (brine shrimp) naupili larvae, daily or 3 times per week and rinsed with fresh medium each day to remove uneaten larvae and debris. Whole organisms may be sectioned surgically, with a blade or fine glass knife, or disrupted mechanically by, for example, vigorous vortex and sonication. Stinging cells are isolated following disruption by separation on 5% Percoll (Technau U et al PNAS USA 2000; 97: 12127-31), or by continuous flow centrifugation using a zonal rotor. Stinging capsules are isolated by homogenizing whole Hydra in $H_2O$, shaking over ice with an equal volume of Percoll and centrifugation at 5000 rpm. Isolated, precipitated capsules are then resuspended in $H_2O$.

The stinging cells generated according to the teachings of the present invention can be used per se by applying one or more stinging cells expressing the therapeutic, cosmetic or diagnostic agent to an outer surface of the tissue (e.g., skin). Following application, the stinging cells are triggered (as is further described hereinbelow) and the therapeutic or the cosmetic agent is thereby delivered by the tubule into the tissue. Triggering the activation of the stinging cell thus leads to the subsequent transdermal/intradermal, transmucosal, transmembranal or transcuticular delivery of the expressed therapeutic or cosmetic agent.

It will be appreciated that in the case of agents which are expressed and targeted to the stinging capsules, the method of delivery of the present invention can further include isolation of stinging capsules following expression of the agent from the exogenous sequences and utilization of isolated capsules for agent delivery. Methods of isolating stinging capsules from stinging cells are detailed hereinabove.

Thus, according to the teachings of the present invention isolated and optionally pretreated stinging cells or capsules can be utilized for delivering a therapeutic or cosmetic agent expressed thereby into a tissue region of an individual. Preparation of such delivery devices is described in detail in Example 1 of the Examples section, which follows.

To stabilize the stinging cell(s) and to possibly enhance triggering efficiency, the transformed stinging cells of the present invention are preferably included in a pharmaceutical composition.

Thus, according to another aspect of the present invention there is provided a pharmaceutical composition, which includes, as an active ingredient, at least one stinging cell expressing a therapeutic, cosmetic or diagnostic agent and a pharmaceutically acceptable carrier.

Hereinafter, the phrase "pharmaceutically acceptable carrier" refers to a carrier, which does not cause significant irritation to the individual treated and does not abrogate the biological activity and properties of the active ingredient.

Preferably, the pharmaceutically acceptable carrier does not affect the ability of the stinging cells to discharge following triggering although in some instances, a pharmaceutically acceptable carrier which inhibits triggering mediated by tissue contact can also be utilized by the present invention.

The pharmaceutical composition of the present invention preferably includes a pharmaceutically acceptable carrier, which is formulated for topical, transmucosal or transnasal applications.

For topical application, the stinging cell(s) may be suspended in hydrophilic or hydrophobic-based carrier such as a gel suitable for topical applications.

For topical, transmucosal or transnasal administration, the stinging cells can be conveniently delivered in the form of drops or an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount.

In any case, application of the composition to, for example, a skin region leads to subsequent contact between the stinging cell(s) and the skin of the individual which contact triggers discharge of the stinging cells and delivery of the active ingredient into for example, an epidermis or dermis tissue region of the individual.

Although, for some applications, contact mediated discharge suffices, such activation can be inefficient since it enables discharge of only the portion of stinging cells or capsules, which come into physical contact with the tissue following application.

To enable a more efficient and consistent discharge and thus delivery of the active agent, the pharmaceutical composition of the present invention can include a pharmaceutically acceptable carrier which inhibits discharge of the stinging cell(s) upon tissue contact skin contact). In such cases, the pharmaceutical composition also includes a chemical activator, such as, for example NaSCN or EGTA, which can be applied prior to, or following, application of the pharmaceutical composition and which triggers discharge of the stinging cells. Such chemical activation of discharge is advantageous since it allows for simultaneous discharge of most if not all of the stinging cells of the pharmaceutical composition.

According to the teachings of the present invention, the stinging cells described above can also be utilized in a delivery device useful for delivering a therapeutic or cosmetic agent expressed therein into a tissue region of an individual.

Thus, as specifically shown in FIG. 2 and according to yet another aspect of the present invention there is provided a delivery device, which is referred to herein as device 10.

Device 10 includes at least one stinging cell 12 (several are shown). Upon discharge, stinging cell 12 is capable of delivering a therapeutic, cosmetic or diagnostic agent expressed thereby into a tissue region (as described hereinabove). Device 10 further includes a support 14, which serves for supporting stinging cell 12 and for applying stinging cell 12 to an outer surface of the tissue region into which delivery is desired.

Support 14 can be, for example, a patch, a foil, a plaster or a film or any material capable of supporting stinging cell(s) 12 in a manner suitable for application to, for example, a skin region of the individual.

Stinging cells 12 can be secured to support 14 via, for example, biological glue (e.g. BIOBOND™), polylysine, a mesh support or the like.

Discharge of stinging cell(s) 12 can be activated upon contact with tissue as described above. For example, following application of device 10, pressure can be exerted on support 14 thus forcing contact between stinging cells 12 and the tissue region thereby activating discharge. Alternatively, discharge can be activated by a mechanism 16 included within device 10.

Mechanism 16 can be an electrical or chemical activating mechanism which when activated by a physician or by the individual to be treated, triggers simultaneous discharge of stinging cell(s) 12 preferably in a rapid and uniform manner.

It will be appreciated that device 10 can be easily adapted for use with isolated stinging capsules of the present invention in addition to, or in place of, the stinging cells 12.

Chemical triggering can be mediated by substances such as free and conjugated N-acetylated sugars or low molecular weight amino compounds which are known to be detected by at least two classes of stinging cell chemoreceptors.

Sodium thiocyanate (NaSCN) and sodium citrate can also be used to trigger discharge of cnidocysts. In addition, Lubbock and Amos (1981) have shown that isolated cnida (cnidocysts) can discharge normally when placed in buffered EGTA or 10 mM citrate solution; Weber (1989) demonstrated the effect of dithioerthritol or proteases on discharging isolated cnida and Hidaka (1993) discussed various agents which can trigger cnida discharge.

Electrical triggering can be achieved via an electrical pulse of 30 microseconds of approximately 20-30 Volts as is further described in the literature (Holstein and Tardent 1984; Tardent and Holstein 1982).

As mentioned hereinabove, the present invention can be utilized to deliver a variety of therapeutic agents. Such therapeutic agents combined with the effective delivery obtainable via stinging cells can be utilized to treat a variety of disorders.

Examples of disorders which can be treated by the present invention include, but are not limited to osteoporosis which can be treated by delivery of calcitonin, insulin dependent diabetes mellitus (IDDM) which can be treated by insulin, multiple sclerosis which can be treated by interferon beta-1 (IFN beta-1) and congestive heart failure, which can be treated by human growth hormone (somatostatin, hGH) (see U.S. Pat. Nos. 6,334,856 and 6,329,342 to Allen et al and Kauffman et all, respectively).

The stinging cells of the present invention can also be utilized for vaccination. Polypeptide antigens expressed within the stinging cells can be delivered to specialized immune cells underlying the skin or into blood circulation (as described above).

Absorption into the blood stream following transdermal delivery will most likely result in transport of the antigen to the phagocytic cells of the liver, spleen, and bone marrow. Since such cells serve as antigen presenting cells, a strong immunogenic response will be elicited leading to effective immunization.

Thus, the present invention overcomes the limitations of prior art devices and methods while providing a safe, efficient and contamination risk free method for delivering agents across epidermal mucosal or membranal barriers.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non-limiting fashion.

Generally, the nomenclature used herein and the laboratory procedures utilized in the present invention include molecular, biochemical, and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); all of which are incorporated by reference as if fully set forth herein. Other general references are provided throughout this document. The procedures therein are believed to be well known in the art and are provided for the convenience of the reader. All the information contained therein is incorporated herein by reference.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Construction of the Plasmid pActHGH

HGH Coding Sequence

The construction of an expression vector suitable for use with the present invention is carried out as follows: the coding sequence of human growth hormone hGH (SEQ ID NO.: 1) is amplified by PCR using gene specific primers (SEQ ID NOs: 2 and 3) which include endonuclease restriction sequences (Bam HI and Eco RI). The resultant PCR product includes a 601 by sequence which encodes the mature hGH.

Expression Vector

The eukaryotic expression vector pSG5, shown in FIG. 1, is used for cloning of the PCR product described above. This expression vector contains an SV40 and T7 promoter region separated by a beta globin intron followed by multiple restriction sites, an SV40 transcription termination sequence and poly-A signal, as well as fl origin of replication and ampicillin resistance gene for bacterial amplification.

E. coli TOP 10F' calcium-competent cells (Invitrogen, Co. San Diego, Calif., USA) are transformed with the plasmids pSG5. The preparation of calcium-competent bacteria and the transformation are carried out in accordance with the protocols described by Sambrook et al. (1989). Subsequently, colonies of bacteria carrying plasmid pSG5 are picked and grown in 1 L of LB broth (1% Tryptone, 0.5% Sodium Chloride and 1% Dextrose). Plasmid DNA is isolated by lysing the cells with TRITON X-100 followed by ultracentrifugation in cesium a chloride density gradient (Cab-Barrera and Barrera-Saldana, 1988).

Digestion of pSG5 and the Amplified hGH PCR Product

The digestion of pSG5 and the amplified hGH PCR products with enzymes Eco RI and Bam HI are performed separately, with 10 μg DNA per reaction, using 20 Units of each enzyme in a 50 μl reaction volume containing the compatible buffer E, according to manufacturers instructions (Promega Corp, Madison, Wis.).

Digestion is verified by analyzing 1 μl aliquots by means of electrophoresis on a 1% agarose gel. Once the above mentioned preparative digestions is complete, preparative electrophoresis is performed on a 1% agarose gel using 25 μl of each digestion reaction, followed by staining with ethidium bromide 2 µg/ml in TBE (Tris-Boric Acid-EDTA buffer). The 607 by fragments from the digestion of the amplified hGH and the 4094 by fragment from the digestion of pSG5 with Eco RI and Bam HI are recovered from the gel by cutting the corresponding bands with the aid of a surgical knife. The fragments are extracted from the agarose matrix using the GENECLEAN II Kit (Bio 101, Inc., Calif., USA) and stored in TE buffer (10 m Tris-HCl, 1 mm EDTA, pH=8) at −20° C. until use. Prior to the ligation reaction, these fragments are annealed by heating in TE buffer at 80° C. for 5 minutes and cooling slowly to room temperature.

The digested and purified hGH PCR product is ligated into the digested pSG5 expression vector using a T4 ligase (Promega Corp., Madison, Wis.) following the manufacturers instructions.

Analysis of the pSGHGH Carrier Clones

Competent DH5α E. coli cells (Invitrogen, Co. San Diego, Calif., USA) are transformed with an aliquot of the ligation reaction using a $CaCl_2$ transformation technique and the resultant transformants are grown on an LB-agar ampicillin plate.

Twenty of the colonies obtained from the transformation (ampillicin resistant) are picked for individual inoculation in tubes with 4 ml of LB broth with ampicillin (100 mg/L). These are incubated and shaken at 37° C. for 18 hours. Subsequently, plasmid DNA is isolated from 2 ml of each culture, using the alkaline method described by Sambrook et al. (1989). The plasmid DNA isolated in each of the clones is digested with BamHI and EcoRI in order to detect the 607 by insert fragment by electrophoresis on a 0.8% agarose gel. The clones that show the expected insert size are further characterized via DNA sequencing using plasmid specific sequencing primers. Plasmids bearing accurately oriented, full sized hGH inserts are termed pSGHGH (FIG. 3).

Construction of the Plasmid pActHGH

Plasmid pActHGH is an expression vector containing the putative Hydra actin gene promoter upstream (5') of the hGH coding sequence of pSGHGH. Hydra actin promoter DNA is prepared by primer extension and PCR amplification of Hydra genomic DNA, using gene-specific forward and reverse primers synthesized from the chicken actin gene promoter sequence (SEQ ID NO.: 4) (SEQ ID NOs.: 5 and 6), containing Eco RI nuclease sequences to allow cloning into the EcoRI site immediately upstream of the hGH start codon, which is preserved by eliminating the chicken actin ATG sequence (b 1276-1278) from the reverse primer (SEQ ID NO 6). Following PCR amplification appropriate sized PCR products are identified by gel electrophoresis, isolated, purified and digested by Eco RI as described for the pSG5 plasmid and hGH coding sequence hereinabove. Ligation of the amplified, purified Hydra promoter sequence DNA into the Eco RI site of pSGHGH creates plasmids with the Hydra actin promoters in two opposing orientations. Bacteria transformed with these plasmids are grown on agar as described for pSGHGH above, and clones that show the expected size plasmids on gel electrophoresis are further characterized by digestion with additional endonucleases, and comparison of the fragments generated with computerized analysis of the plasmid sequence pSGHGH and primer sequences (SEQ ID NOs 5 and 6) (mbs seqCUTTER, JustBio website Homepage). A clone that shows the expected restriction pattern is selected for large-scale plasmid DNA preparation, providing a source of good quality plasmids with which to perform the transformation of stinging cells. The resultant plasmid is designated pActHGH (FIG. 3).

Example 2

Hydra Transformation and Expression of hGH and Luciferase in Cnidocysts

Once the identity of the vector pActHGH has been ensured, plasmid DNA is prepared for co-transformation of Hydra vulgaris by electroporation along with expression vector pGL-2 Control (Promega Corp, Madison Wis.), which includes the reporter firefly luciferase coding sequence "luc", SV-40 promoter and enhancer sequences.

Hydra Culture Conditions

Hydra are cultured according to methods well known in the art (for exhaustive discussion of methods see Hydra: Research Methods; H. M. Lenoff, 1983, Plenum Press). Hydra culture medium contains 1 mM $CaCl_2$, 1 mM Tris-HCl, pH 7.6, 1 mM $NaHCO_3$, 0.1 mM KCl and 0.1 mM $MgCl_2$. Cultures of Hydra are maintained in glass or plastic containers. The Hydra are fed freshly hatched Artemia (brine shrimp) naupili larvae, daily or 3 times per week and Hydra are rinsed with fresh medium each day to remove uneaten larvae and debris.

Hydra Transformation

Hydra are concentrated by centrifugation at 200 rpm for 5 minutes (centrifuge IEC CENTRA MP4R Rotor 854), and washed twice, first in 10 ml of sterile Hydra medium, and then with 10 MILLI-Q water (purified water from a MILLI-Q water system, obtained from Millipore) and gently resuspended in 0.5 ml sterile water. 100 µl of this Hydra suspension is mixed with 250 ng of plasmid DNA, containing equal amounts of pSGHGH1 and pGL-2, and transferred to 0.4 cm electroporation micro-chambers (BioRad, Melville, N.Y.). 2.5 µl of 1 mg/ml DEAE-dextran is added and mixed immediately prior to electroporation to create a two phase system for enhanced efficiency, as described by Petri, Jr et al (U.S. Pat. No. 5,891,634 to Petri, Jr et al). Efficient electroporation conditions are determined by electroporation within a range of pulses from 150 to 600V/cm, 500 using a Gene Pulser (BioRad, Melville, N.Y.). The electroporated Hydra are then diluted in 10 ml culture medium, incubated at 18 degrees C. for 24 hours, washed to remove excess plasmid DNA and assayed for expression of the transfected DNA by Luminometer.

Luciferase Assay

Transfected Hydra in Hydra medium are centrifuged at 200 g for 5 minutes and washed one time in PBS, pH 7.5. The pelleted Hydra is resuspended in an equal amount of Hydra buffer containing 1% Triton X-100. Samples are immediately frozen at −20° C. for a minimum of one hour, thawed on ice for 10 minutes, vigorously vortexed for 2 minutes, centrifuged briefly to pellet debris, and returned on ice for an additional 10 minutes. After warming to room temperature for 10 minutes, 20 µl of the Hydra lysate is assayed in 100 µl of luciferase assay reagent (20 mM Tricin, 1.07 mM $(MgCO_3)_4Mg(OH)_2 5H_2O$, 2.67 mM $MgSO_4$, 0.1 mM EDTA, 33.3 mM DTT, 270 µM coenzyme A, 470 µM luciferin, 530 µM ATP, final pH 7.8) using a Turner Luminometer Model TD-20e (Promega, Madison Wis.). Background luminescence on the luminometer is calibrated to zero immediately prior to all assays with Hydra electroporated without plasmid. Luciferase activity is calculated from a standard curve obtained before each experiment using the same substrate and exogenous firefly luciferase (approximately $10^7$ luciferase light units/mg luciferase, Boehringer Mannheim Biochemica).

Luciferase positive lysate samples are then assayed for the presence of hGH protein by ELISA of cell lysates using commercially available hGH detection kits (Roche Applied Sciences, N.J.).

Example 3

Testing Transformed Cnidocysts for the Ability to Deliver Growth Hormone When Activated Having determined optimum, reproducible conditions for transformation of Hydra by electroporation, and expression of the pActHGH hGH coding sequence, the ability of cnidocysts from the transformed Hydra to deliver the cloned hGH protein is assayed by controlled activation and delivery of the hGH into a gel substrate.

Cnidocytes are isolated from whole Hydra containing the pActHGH plasmid as described hereinabove, after recovery from electroporation (24 hours) and washing in culture medium by centrifugation at 200 g. The cnidocytes are then suspended in 0.5 ml $H_2O$, and 50 µl aliquots immobilized onto poly L-lysine-coated (0.1M) glass coverslips, as described by Wennemuth (Wennemuth G, et al Andrologia 1998; 30:141-6). The immobilized cnidocytes are then applied to 15% polyacrylamide gel, location marked with dye, and activated by addition of sodium citrate (100 mM). Control supports have cnidocytes from control electroporated Hydra (no plasmid), cnidocytes from Hydra transformed with pGL-2 Control alone, and unactivated, cnidocytes from pActHGH-transformed Hydra.

Following activation, release of tubules and removal of the glass supports, the gel is washed free of adhering cnidocytes in Tris-SDS buffer, each portion of the gel in contact with the cnidocytes excised separately, minced and the protein contents of each sample eluted and concentrated by the Nanosep® Centrifugal Elution System (Pall Filtron, Northborough, Mass.), according to manufacturers instructions. Samples of the eluted proteins are then further separated by SDS-PAGE, and electroblotted onto nitrocellulose using a Fisher SemiDry Blotting apparatus according to manufacturers instructions (Fisher Scientific, Springfield N.J.). Immunoreactive hGH protein bands are detected using rabbit polyclonal anti hGH and goat HRP-conjugated anti-rabbit antibodies, according to manufacturers instructions (Biogenex, San Ramon Calif.).

Example 4

GFP Expression in Hydra Capsules

Hydra vulgaris were maintained at 18° C. in hydra medium A (1 mM $CaCl_2$, 1 mM Tris-HCl PH 7.6-7.8, 0.1 mM KCl, 0.1 mM $MgCl_2$, 1 mM NaHCO3) and fed three times a week with freshly hatched Artemia. Twenty four hours before transfection feeding was stopped and the hydra were washed three times in hydra medium B (1 mM $CaCl_2$, 0.1 mM KCl, 0.1 mM $MgCl_2$, 1 mM NaHCO3 PH 7.8) placed in hydra medium B including chilled 0.01% heptanol and 0.5% urethane and hydra heads and legs were dissected. Polyps were pulsed with Bio-Rad Gene Pulser Xcell™ System (Bio-Rad). Electroporation conditions were as previously described by Bosch et al, (Differentiation, 40 140-147 2002). Briefly, polyps were chilled for 1 hour on ice, placed in 0.2 cm chilled cuvette with 0.2 ml hydra medium B containing 15 µg supercoiled plasmid DNA. Electroporation was carried out under a field strength of 1.25 Kv/cm (Voltage-250v, Capacitance 25 µF, Resistance 300Ω, Pulse length ~5 msec). Immediately following electroporation the hydra were transferred into 10 ml of hydra medium B which was supplemented with 20% hyperosmotic dissociation medium (6 mM $CaCl_2$, 1.2 mM $MgSO_4$, 3.6 mM KCl, 12.5 mM TES PH 6.9, 6 mM sodium pyruvate 6 mM sodium citrate, 6 mM glucose) (Gierer et al. Nat New Biol 239:98-101 1972). Twenty four hours following electroporation the medium was replaced with hydra medium B.

The plasmid for transfection contained Chicken β-Actin promoter fused to a sequence encoding the AeNa +pro peptide (Anderluh et al. BBA 1476 372-376; 2000) positioned up stream of an EGFP encoding sequence (BD Biosciences Clontech). Following transformation, the hydra was observed under a fluorescent microscope (Zeiss Axioskop 40 microscope, filter set 09 magnification X400) 48 hours following electroporation. As shown in FIG. 4, AeNa +pro-GFP expressed from the plasmid described above was actively transported into the capsule of hydra stinging cells.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and GenBank Accession numbers disclosed therein and/or mentioned in this specification are herein incorporated in their entirety by reference into the specification, to the same extent as if each individual publication, patent, patent application or GenBank Accession number was specifically and individually indicated to be incorporated herein by reference. In addition, citation or identification of any reference in this application shall not be construed as an admission that such reference is available as prior art to the present invention.

REFERENCES

Additional References Cited Hereinabove

1. Anderson, C. L., Canning, E. U., and Okamura, B. (1998). "A triploblast origin for Myxozoa?" *Nature,* 392(6674), 346-7.
2. Brennecke, T., Gellner, K., and Bosch, T. C. (1998). "The lack of a stress response in Hydra oligactis is due to reduced hsp70 mRNA stability." *Eur J Biochem,* 255(3), 703-9.
3. Godkenecht, A., and Tardent, P. (1988). "Discharge and mode of action of the tentacular nematocysts of *Anemonia sulcata* (Antozoa: Cnidaria)." *Marine Biology,* 100, 83-92.
4. Heeger, T., Moller, H., and Mroweitz, U. (1992). "Protection of human skin against jellyfish (*Cyanea capillata*) stings." *Marine Biology,* 113, 669-678.
5. Hidaka, M. (1992). "Effects of Ca+ on the volume of nematocysts isolated from acontia of the sea anemone *Calliactis tricolor*." *Comp Biochem Physiol,* 101A(4), 737-741.
6. Hidaka, M. (1993). "Mechanism of nematocyst discharge and its cellular control." *Advances in Comparative and Environmental Physiology,* 15, 45-76.
7. Holstein, T., and Tardent, P. (1984). "An ultrahigh-speed analysis of exocytosis: nematocyst discharge." *Science,* 223(4638), 830-3.
8. Lotan, A., Fishman, L., Loya, Y., and Zlotkin, E. (1995). "Delivery of a nematocyst toxin *Nature,* 375(6531), 456.
9. Lotan, A., Fishman, L., and Zlotkin, E. (1996). "Toxin compartmentation and delivery in the Cnidaria: the nematocyst's tubule as a multiheaded poisonous arrow." *J Exp Zool,* 275(6), 444-51.

10. Lubbock, R. (1979). "Chemical recognition and nematocyte excitation in sea anemone." *J. exp. Biol.,* 83, 283-292.
11. Lubbock, R., and Amos, W. B. (1981). "Removal of bound calcium from nematocyst contents causes discharge." *Nature,* 290(5806), 500-1.
12. Mariscal, R. N. (1974). *Coelenterate biology: reviews and new perspectives,* Academic Press, New York.
13. Siddall, M. E., Martin, D. S., Bridge, D., Desser, S. S., and Cone, D. K. (1995). "The demise of a phylum of protists: phylogeny of Myxozoa and other parasitic cnidaria." *J Parasitol,* 81(6), 961-7.
14. Smothers, J. F., von Dohlen, C. D., Smith, L. H., Jr., and Spall, R. D. (1994). "Molecular evidence that the myxozoan protists are metazoans." *Science,* 265(5179), 1719-21.
15. Tardent, P. (1995). "The cnidarian cnidocyte, a high-tech cellular weaponry." *BioEssays,* 17(4), 351-362.
16. Tardent, P., and Holstein, T. (1982). "Morphology and morphodynamics of the stenotele nematocyst of Hydra attenuata Pall. (Hydrozoa, Cnidaria)." *Cell Tissue Res,* 224 (2), 269-90.
17. Thorington, G. U., and Hessinger, D. A. (1988). "Control of cnida discharge: I. evidence for two classes of chemoreceptor." *Biol. Bull.,* 174, 163-171.
18. Watson, G. M., and Hessinger, D. (1989). "Cnidocyte mechanoreceptors are tuned to the movements of swimming prey by chemoreceptors." *Science,* 243, 1585-1591.
19. Watson, G. M., and Hessinger, D. A. (1992). "Receptors for N-acetylated sugars may stimulate adenylate cyclase to sensitize and tune mechanoreceptors involved in triggering nematocyst discharge." *Exp Cell Res,* 198(1), 8-16.
20. Weber, J. (1989). "Nematocysts (stinging capsules of Cnidaria) as Donnan-potential-dominated osmotic systems." *Eur J Biochem,* 184(2), 465-76.
21. Westfall, J. A., Bradbury, P. C., and Townsend, J. W. (1983). "Ultrastructure of the dinoflagellate Polykrikos. I. Development of the nematocyst-taeniocyst complex and morphology of the site for extrusion." *J Cell Sci,* 63, 245-61.
22. Gierasch, (1989). "Signal sequences". Biochemistry, 269: 923-930.
23. Von Heijne (1990). "The signal peptide". J. Membrane Biol., 115: 195-201.
24. Rapoport, (1992). "Transport of proteins across the endoplasmic reticulum membrane". Science, 258: 931-936.
25. Engel, Pertz, Fauser, Engel, David, Holstein. (2001). "A switch in disulfide linkage during minicollagen assembly in Hydra nematocysts". EMBO 20:3063-73.
26. Holstein, (1981). "the morphogenesis of nematocytes in Hydra and Forskalia: ultrastructural study". J. Ultrastruct. Res. 75: 276-290.
27. Nielsen, Engelbrecht, Brunak, von Heijne (1997). "Identification of prokaryotic and eukaryotic signal peptides and prediction of their cleavage sites. Protein Engineering 10:1-6.
28. Krogh (1998) In Proceeding of the Sixth International Conference on Intelligent Systems for Molecular Biology (ISMB 6), AAAI Press, Menlo Park, Calif., pp. 122-130.

---

What is claimed is:

1. A method of generating a stinging cell expressing a therapeutic, cosmetic or diagnostic agent, the method comprising:
   a) transforming a stinging-cell-bearing organism with a nucleic acid construct comprising an exogenous polynucleotide comprising:
      i) an exogenous polynucleotide encoding the therapeutic, cosmetic or diagnostic agent; and
      ii) a promoter directing expression of said agent in said stinging cell; and
   b) isolating a stinging cell expressing said agent from said transformed organism,
   thereby generating at least one stinging cell expressing said therapeutic, cosmetic or diagnostic agent.

2. The method of claim 1, wherein said stinging cell is selected from the group consisting of a cnidocyte, a nematocyte, a spirocyte and a ptychocyte.

3. The method of claim 1, wherein said organism is of a class selected from the group consisting of Anthozoa, Hydrozoa and Scyphozoa.

4. The method of claim 1, wherein said organism is of a phylum selected from the group consisting of Cnidaria, Dinoflagellata and Myxozoa.

5. The method of claim 1, further comprising isolating a stinging capsule out of said stinging cell in which said therapeutic, cosmetic or diagnostic agent has been accumulated following said transformation.

6. The method of claim 1, wherein said agent is a ribozyme and/or antisense polynucleotide.

7. The method of claim 1, wherein said agent is a polypeptide.

8. The method of claim 1, wherein said nucleic acid construct further comprises a polynucleotide sequence being translationally fused with said polynucleotide and encoding a signal peptide for transport of said agent into a capsule of said stinging cell.

9. The method of claim 1, wherein said organism is of the class Anthozoa.

10. The method of claim 1, wherein said stinging cell is a nematocyst.

11. The method of claim 1, wherein transforming said organism is affected via a method selected from the group consisting of transforming whole polyps, transforming an isolated budding region of the polyp, transforming isolated endoderm of the organism, transforming isolated ectoderm of the organism, transforming cell suspensions of cells which can form fresh polyps from aggregates, and transforming fertilized eggs of said organism.

12. The method of claim 1, wherein transforming said organism is affected via transforming whole polyps.

13. The method of claim 1, wherein said promoter is a cnidarian promoter.

14. The method of claim 13, wherein said promoter is an endogenous promoter of said organism.

15. The method of claim 8, wherein said signal peptide is a cnidarian signal peptide.

* * * * *

SEQUENCE LISTING

```
<160> NUMBER OF SEQ ID NOS: 17

<210> SEQ ID NO 1
<211> LENGTH: 654
<212> TYPE: DNA
<213> ORGANISM: Homo sapiens

<400> SEQUENCE: 1
atggctacag gctcccggac gtccctgctc ctggcttttg gcctgctctg cctgccctgg      60
cttcaagagg gcagtgcctt cccaaccatt cccttatcca ggcttttga caacgctatg     120 ctccgcgccc atcgtctgca ccagctggcc tttgacacct accaggagtt tgaagaagcc     180
tatatcccaa aggaacagaa gtattcattc ctgcagaacc cccagacctc cctctgtttc     240
tcagagtcta ttccgacacc ctccaacagg gaggaaacac aacagaaatc caacctagag     300
ctgctccgca tctccctgct gctcatccag tcgtggctgg agcccgtgca gttcctcagg     360
agtgtcttcg ccaacagcct ggtgtacggc gcctctgaca gcaacgtcta tgacctccta     420
aaggacctag aggaaggcat ccaaacgctg atggggaggc tggaagatgg cagccccgg     480 actgggcaga tcttcaagca gacctacagc aagttcgaca caaactcaca caacgatgac     540
gcactactca agaactacgg gctgctctac tgcttcagga aggacatgga caaggtcgag     600
acattcctgc gcatcgtgca gtgccgctct gtggagggca gctgtggctt ctag           654

<210> SEQ ID NO 2
<211> LENGTH: 26
<212> TYPE: DNA
<213> ORGANISM: Artificial sequence
<220> FEATURE:
<223> OTHER INFORMATION: Synthetic single strand oligonucleotide
```

```
<400> SEQUENCE: 2
gtccgggagc ctgtagccat gaattc                                        26

<210> SEQ ID NO 3
<211> LENGTH: 26
<212> TYPE: DNA
<213> ORGANISM: Artificial sequence
<220> FEATURE:
<223> OTHER INFORMATION: Synthetic single strand oligonucleotide

<400> SEQUENCE: 3
agggcagctg tggcttctag ggatcc                                        26

<210> SEQ ID NO 4
<211> LENGTH: 1278
<212> TYPE: DNA
<213> ORGANISM: Gallus gallus

<400> SEQUENCE: 4
tcgaggtgag ccccacgttc tgcttcactc tccccatctc ccccccctcc ccacccccaa    60
ttttgtattt atttattttt taattatttt gtgcagcgat ggggcgggg gggggggggg   120 cgcgcgccag gcggggcggg gcgggcgag gggcggggcg gggcgaggcg gagaggtgcg   180
gcggcagcca atcagagcgg cgcgctccga aagtttcctt ttatggcgag gcggcggcgg   240
cggcggccct ataaaagcg aagcgcgcgg cgggcgggag tcgctgcgtt gccttcgccc    300
cgtgccccgc tccgcgccgc ctcgcgccgc ccgccccggc tctgactgac cgcgttactc   360
ccacaggtga gcgggcggga cggcccttct cctccgggct gtaattagcg cttggtttaa   420
tgacggctcg tttctttttct gtggctgcgt gaaagcctta aagggctccg ggagggccct   480
ttgtgcgggg gggagcggct cggggggtgc gtgcgtgtgt gtgtgcgtgg ggagcgccgc   540
gtgcggcccg cgctgccggg cggctgtgag cgctgcgggc gcggcgcggg gctttgtgcg   600
ctccgcgtgt gcgcgagggg agcgcggccg ggggcggtgc cccgcggtgc gggggggctg   660 cgagggggaac aaaggctgcg tgcggggtgt gtgcgtgggg gggtgagcag ggggtgtggg   720
cgcggcggtc gggctgtaac ccccccctgc accccccctcc ccgagttgct gagcacggcc   780
cggcttcggg tgcggggctc cgtgcggggc gtggcgcggg gctcgccgtg ccgggcgggg   840
ggtggcggca ggtgggggtg ccgggcgggg cggggccgcc tcgggccggg gagggctcgg   900
gggaggggcg cggcggcccc ggagcgccgg cggctgtcga ggcgcggcga gccgcagcca   960 ttgccttta tggtaatcgt gcgagagggc gcagggactt cctttgtccc aaatctggcg   1020
gagccgaaat ctgggaggcg ccgccgcacc ccctctagcg ggcgcgggcg aagcggtgcg   1080
gcgccggcag gaaggaaatg ggcggggagg gccttcgtgc gtcgccgcgc cgccgtcccc   1140
ttctccatct ccagcctcgg ggctgccgca ggggacggc tgccttcggg ggggacgggg   1200
cagggcgggg ttcggcttct ggcgtgtgac cggcggggtt tatatcttcc cttctctgtt   1260
cctccgcagc cagccatg                                                1278

<210> SEQ ID NO 5
<211> LENGTH: 26
<212> TYPE: DNA
<213> ORGANISM: Artificial sequence
<220> FEATURE:
<223> OTHER INFORMATION: Synthetic single strand oligonucleotide

<400> SEQUENCE: 5
gaacgtgggg ctcacctcga gaattc                                        26
```

```
<210> SEQ ID NO 6
<211> LENGTH: 26
<212> TYPE: DNA
<213> ORGANISM: Artificial sequence
<220> FEATURE:
<223> OTHER INFORMATION: Synthetic single strand oligonucleotide

<400> SEQUENCE: 6
ggctggctgc ggaggaacag gaattc                                          26

<210> SEQ ID NO 7
<211> LENGTH: 19
<212> TYPE: PRT
<213> ORGANISM: Actinia equina
<220> FEATURE:
<221> NAME/KEY: misc_feature
<223> OTHER INFORMATION: Sodium channel Inhibitor precursor signal
      peptide
<220> FEATURE:
<221> NAME/KEY: misc_feature
<222> LOCATION: (1)..(4)
<223> OTHER INFORMATION: N-region, positively charged
<220> FEATURE:
<221> NAME/KEY: misc_feature
<222> LOCATION: (5)..(14)
<223> OTHER INFORMATION: H-region, hydrophobic
<220> FEATURE:
<221> NAME/KEY: misc_feature
<222> LOCATION: (15)..(19)
<223> OTHER INFORMATION: C-region, neutral but polar
<220> FEATURE:
<221> NAME/KEY: misc_feature
<222> LOCATION: (19)..(19)
<223> OTHER INFORMATION: Cleavage site

<400> SEQUENCE: 7

Met Ala Asn Arg Leu Met Ile Val Phe Ala Ala Val Phe Leu Ala Leu
1               5                   10                  15

Ala Ser Ala

<210> SEQ ID NO 8
<211> LENGTH: 28
<212> TYPE: PRT
<213> ORGANISM: Actinia equina
<220> FEATURE:
<221> NAME/KEY: misc_feature
<223> OTHER INFORMATION: Sodium channel Inhibitor precursor signal
      peptide
<220> FEATURE:
<221> NAME/KEY: misc_feature
<222> LOCATION: (1)..(4)
<223> OTHER INFORMATION: N-region, positively charged
<220> FEATURE:
<221> NAME/KEY: misc_feature
<222> LOCATION: (5)..(14)
<223> OTHER INFORMATION: H-region, hydrophobic
<220> FEATURE:
<221> NAME/KEY: misc_feature
<222> LOCATION: (15)..(19)
<223> OTHER INFORMATION: C-region, neutral but polar
<220> FEATURE:
<221> NAME/KEY: misc_feature
<222> LOCATION: (19)..(19)
<223> OTHER INFORMATION: Cleavage site

<400> SEQUENCE: 8

Met Ala Asn Arg Leu Met Ile Val Phe Ala Ala Val Phe Leu Ala Leu
1               5                   10                  15

Ala Ser Ala Asp Glu Asp Val Asp Ile Ala Lys Arg
            20                  25
```

```
<210> SEQ ID NO 9
<211> LENGTH: 23
<212> TYPE: PRT
<213> ORGANISM: Heteractis magnifica
<220> FEATURE:
<221> NAME/KEY: misc_feature
<223> OTHER INFORMATION: K-channel toxin precursor
<220> FEATURE:
<221> NAME/KEY: misc_feature
<222> LOCATION: (1)..(6)
<223> OTHER INFORMATION: N-region, positively charged
<220> FEATURE:
<221> NAME/KEY: misc_feature
<222> LOCATION: (7)..(18)
<223> OTHER INFORMATION: H-region, hydrophobic
<220> FEATURE:
<221> NAME/KEY: misc_feature
<222> LOCATION: (19)..(23)
<223> OTHER INFORMATION: C-region, neutral but polar
<220> FEATURE:
<221> NAME/KEY: misc_feature
<222> LOCATION: (23)..(23)
<223> OTHER INFORMATION: Cleavage site

<400> SEQUENCE: 9

Met Ala Lys Ser Gln Met Ile Ala Ala Val Leu Leu Ile Ala Phe Cys
1               5                   10                  15

Leu Cys Val Val Val Thr Ala
            20

<210> SEQ ID NO 10
<211> LENGTH: 16
<212> TYPE: PRT
<213> ORGANISM: Hydra vulgaris
<220> FEATURE:
<221> NAME/KEY: misc_feature
<223> OTHER INFORMATION: N-COL1 mini collagen
<220> FEATURE:
<221> NAME/KEY: misc_feature
<222> LOCATION: (1)..(4)
<223> OTHER INFORMATION: N-region, positively charged
<220> FEATURE:
<221> NAME/KEY: misc_feature
<222> LOCATION: (5)..(14)
<223> OTHER INFORMATION: H-region, hydrophobic
<220> FEATURE:
<221> NAME/KEY: misc_feature
<222> LOCATION: (15)..(16)
<223> OTHER INFORMATION: C-region, neutral but polar
<220> FEATURE:
<221> NAME/KEY: misc_feature
<222> LOCATION: (16)..(16)
<223> OTHER INFORMATION: Cleavage site

<400> SEQUENCE: 10

Met Ala Met Arg Leu Val Leu Ala Cys Leu Val Leu Gly Val Ala Ala
1               5                   10                  15

<210> SEQ ID NO 11
<211> LENGTH: 20
<212> TYPE: PRT
<213> ORGANISM: Apis mellifera
<220> FEATURE:
<221> NAME/KEY: misc_feature
<223> OTHER INFORMATION: phospholipase A2 signal peptide
<220> FEATURE:
<221> NAME/KEY: misc_feature
<222> LOCATION: (1)..(4)
<223> OTHER INFORMATION: N-region, positively charged
<220> FEATURE:
<221> NAME/KEY: misc_feature
<222> LOCATION: (5)..(15)
<223> OTHER INFORMATION: H-region, hydrophobic
```

```
<220> FEATURE:
<221> NAME/KEY: misc_feature
<222> LOCATION: (16)..(20)
<223> OTHER INFORMATION: C-region, neutral but polar

<400> SEQUENCE: 11

Met Ala Gln Val Val Leu Leu Gly Ser Leu Phe Leu Leu Leu Leu Ser
1               5                   10                  15

Thr Ser His Gly
            20

<210> SEQ ID NO 12
<211> LENGTH: 20
<212> TYPE: PRT
<213> ORGANISM: Adamsia carciniopados
<220> FEATURE:
<221> NAME/KEY: misc_feature
<223> OTHER INFORMATION: Phospholipase A2 signal peptide
<220> FEATURE:
<221> NAME/KEY: misc_feature
<222> LOCATION: (1)..(6)
<223> OTHER INFORMATION: N-region, positively charged
<220> FEATURE:
<221> NAME/KEY: misc_feature
<222> LOCATION: (7)..(17)
<223> OTHER INFORMATION: H-region, hydrophobic
<220> FEATURE:
<221> NAME/KEY: misc_feature
<222> LOCATION: (18)..(20)
<223> OTHER INFORMATION: C-region, neutral but polar
<220> FEATURE:
<221> NAME/KEY: misc_feature
<222> LOCATION: (20)..(20)
<223> OTHER INFORMATION: Cleavage site

<400> SEQUENCE: 12

Met Ala Gln Leu Tyr Thr Tyr Phe Phe Thr Phe Ser Leu Val Leu Ile
1               5                   10                  15

Leu Ala Leu Ala
            20

<210> SEQ ID NO 13
<211> LENGTH: 28
<212> TYPE: PRT
<213> ORGANISM: Homo sapiens
<220> FEATURE:
<221> NAME/KEY: misc_feature
<223> OTHER INFORMATION: Erythropoietin
<220> FEATURE:
<221> NAME/KEY: misc_feature
<222> LOCATION: (1)..(10)
<223> OTHER INFORMATION: N-region, positively charged
<220> FEATURE:
<221> NAME/KEY: misc_feature
<222> LOCATION: (11)..(21)
<223> OTHER INFORMATION: H-region, hydrophobic
<220> FEATURE:
<221> NAME/KEY: misc_feature
<222> LOCATION: (22)..(28)
<223> OTHER INFORMATION: C-region, neutral but polar
<220> FEATURE:
<221> NAME/KEY: misc_feature
<222> LOCATION: (28)..(28)
<223> OTHER INFORMATION: Cleavage site

<400> SEQUENCE: 13

Met Ala Gly Val His Glu Cys Pro Ala Trp Leu Trp Leu Leu Leu Ser
1               5                   10                  15

Leu Leu Ser Leu Pro Leu Gly Leu Pro Val Leu Gly
            20                  25
```

```
<210> SEQ ID NO 14
<211> LENGTH: 21
<212> TYPE: PRT
<213> ORGANISM: Homo sapiens
<220> FEATURE:
<221> NAME/KEY: misc_feature
<223> OTHER INFORMATION: Coagulation factor VII
<220> FEATURE:
<221> NAME/KEY: misc_feature
<222> LOCATION: (1)..(8)
<223> OTHER INFORMATION: N-region, positively charged
<220> FEATURE:
<221> NAME/KEY: misc_feature
<222> LOCATION: (9)..(16)
<223> OTHER INFORMATION: H-region, hydrophobic
<220> FEATURE:
<221> NAME/KEY: misc_feature
<222> LOCATION: (17)..(21)
<223> OTHER INFORMATION: C-region, neutral but polar

<400> SEQUENCE: 14

Met Ala Val Ser Gln Ala Leu Arg Leu Leu Cys Leu Leu Leu Gly Leu
1               5                   10                  15

Gln Gly Cys Leu Ala
            20

<210> SEQ ID NO 15
<211> LENGTH: 24
<212> TYPE: PRT
<213> ORGANISM: Homo sapiens
<220> FEATURE:
<221> NAME/KEY: misc_feature
<223> OTHER INFORMATION: Insulin
<220> FEATURE:
<221> NAME/KEY: misc_feature
<222> LOCATION: (1)..(6)
<223> OTHER INFORMATION: N-region, positively charged
<220> FEATURE:
<221> NAME/KEY: misc_feature
<222> LOCATION: (7)..(16)
<223> OTHER INFORMATION: H-region, hydrophobic
<220> FEATURE:
<221> NAME/KEY: misc_feature
<222> LOCATION: (17)..(24)
<223> OTHER INFORMATION: C-region, neutral but polar
<220> FEATURE:
<221> NAME/KEY: misc_feature
<222> LOCATION: (24)..(24)
<223> OTHER INFORMATION: Cleavage site

<400> SEQUENCE: 15

Met Ala Leu Trp Met Arg Leu Leu Pro Leu Leu Ala Leu Leu Ala Leu
1               5                   10                  15

Trp Gly Pro Asp Pro Ala Ala Ala
            20

<210> SEQ ID NO 16
<211> LENGTH: 18
<212> TYPE: PRT
<213> ORGANISM: Homo sapiens
<220> FEATURE:
<221> NAME/KEY: misc_feature
<223> OTHER INFORMATION: Secretin
<220> FEATURE:
<221> NAME/KEY: misc_feature
<222> LOCATION: (1)..(6)
<223> OTHER INFORMATION: N-region, positively charged
<220> FEATURE:
<221> NAME/KEY: misc_feature
<222> LOCATION: (6)..(13)
<223> OTHER INFORMATION: H-region, hydrophobic
```

```
<220> FEATURE:
<221> NAME/KEY: misc_feature
<222> LOCATION: (14)..(18)
<223> OTHER INFORMATION: C-region, neutral but polar
<220> FEATURE:
<221> NAME/KEY: misc_feature
<222> LOCATION: (18)..(18)
<223> OTHER INFORMATION: Cleavage site

<400> SEQUENCE: 16

Met Ala Pro Arg Pro Leu Leu Leu Leu Leu Leu Leu Leu Gly Gly Ser
1               5                   10                  15

Ala Ala

<210> SEQ ID NO 17
<211> LENGTH: 26
<212> TYPE: PRT
<213> ORGANISM: Homo sapiens
<220> FEATURE:
<221> NAME/KEY: misc_feature
<223> OTHER INFORMATION: Growth hormone 1
<220> FEATURE:
<221> NAME/KEY: misc_feature
<222> LOCATION: (1)..(8)
<223> OTHER INFORMATION: N-region, positively charged
<220> FEATURE:
<221> NAME/KEY: misc_feature
<222> LOCATION: (7)..(18)
<223> OTHER INFORMATION: H-region, hydrophobic
<220> FEATURE:
<221> NAME/KEY: misc_feature
<222> LOCATION: (19)..(26)
<223> OTHER INFORMATION: C-region, neutral but polar
<220> FEATURE:
<221> NAME/KEY: misc_feature
<222> LOCATION: (26)..(26)
<223> OTHER INFORMATION: Cleavage site

<400> SEQUENCE: 17

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25
```